(12) United States Patent
Wegener

(10) Patent No.: US 8,317,706 B2
(45) Date of Patent: *Nov. 27, 2012

(54) POST-BEAMFORMING COMPRESSION IN ULTRASOUND SYSTEMS

(75) Inventor: Albert W. Wegener, Portola Valley, CA (US)

(73) Assignee: White Eagle Sonic Technologies, Inc., Santa Clara, CA (US)

( * ) Notice: Subject to any disclaimer, the term of this patent is extended or adjusted under 35 U.S.C. 154(b) by 637 days.

This patent is subject to a terminal disclaimer.

(21) Appl. No.: 12/494,184

(22) Filed: Jun. 29, 2009

(65) Prior Publication Data

US 2010/0331689 A1 Dec. 30, 2010

(51) Int. Cl.
*A61B 8/00* (2006.01)
(52) U.S. Cl. .......................... 600/443; 600/437
(58) Field of Classification Search .................. 600/437, 600/443, 459; 367/103, 104
See application file for complete search history.

(56) References Cited

U.S. PATENT DOCUMENTS

| | | | |
|---|---|---|---|
| 4,751,929 A | 6/1988 | Hayakawa et al. |
| 6,042,545 A | 3/2000 | Hossack et al. |
| 6,315,722 B1 | 11/2001 | Yaegashi |
| 6,855,113 B2 | 2/2005 | Amemiya et al. |
| 7,009,533 B1 | 3/2006 | Wegener |
| 2003/0149362 A1 | 8/2003 | Azuma et al. |
| 2005/0124890 A1 | 6/2005 | Halmann et al. |
| 2005/0148878 A1 | 7/2005 | Phelps et al. |
| 2006/0074320 A1 | 4/2006 | Yoo et al. |
| 2007/0239019 A1 | 10/2007 | Richard et al. |
| 2008/0114246 A1 | 5/2008 | Randall et al. |

FOREIGN PATENT DOCUMENTS

| | | |
|---|---|---|
| JP | 11347033 A | 12/1999 |
| JP | 2005081082 | 3/2005 |
| WO | 9709930 | 3/1997 |
| WO | 0010638 A2 | 3/2000 |
| WO | 0030544 A1 | 6/2000 |

OTHER PUBLICATIONS

PCT Search Report Mailed Jan. 3, 2011 in PCT/US2010/036672, 8 pages.
PCT Search Report Mailed Jan. 26, 2011 in PCT/US2010/039081, 8 pages.
Ruetsch, Greg, et al., "Getting Started with CUDA," Nvidia Corp, Aug. 25-27, 2008, 65 pages.
Seiler, Larry, et al., "Larrabee: A Many-Core x86 Architecture for Visual Computing," ACM Transactions on Graphics, vol. 27, No. 3, Article 18, Aug. 2008, 16 pages.

(Continued)

*Primary Examiner* — Michael Rozanski
(74) *Attorney, Agent, or Firm* — Carolyn Koenig; Haynes Beffel & Wolfeld LLP

(57) ABSTRACT

In an ultrasound imaging system that applies a beamformer to received ultrasound signal samples to form one or more beams represented by arrays of beamformed samples, a method and an apparatus compress each array of beamformed samples independently of the other arrays to form compressed beams. A plurality of analog to digital converters sample multiple analog ultrasound signals produced by a transducer array to provide multiple streams of ultrasound signal samples to the beamformer. The compressed beams are transferred via a digital interface to a signal processor. At the signal processor, the compressed beams are decompressed to form decompressed beams. The signal processor further processes the decompressed beams for diagnostic imaging, such as for B-mode and Doppler imaging, and scan conversion to prepare the resulting ultrasound image for display. This abstract does not limit the scope of the invention as described in the claims.

39 Claims, 24 Drawing Sheets

OTHER PUBLICATIONS

Ali, Murtaza, et al., "Signal Processing Overview of Ultrasound Systems for Medical Imaging," Texas Instruments White Paper SPRAB12, Nov. 2008, 26 pages.

Behar, V., et al., "Parameter optimization of pulse compression in ultrasound imaging system with coded excitation," Ultrasonics, vol. 42 (2004) pp. 1101-1109.

Delgorge, et al., "A Tele-Operated Mobile Ultrasound Scanner Using a Light-Weight Robot," IEEE Trans. Information Technology in Biomedicine, vol. 9, No. 1, Mar. 2005, pp. 50-58.

Delgorge, et al., "Comparative Survey of Ultrasound Images Compression Methods Dedicated to a Tele-Echography Robotic System," 2001 Proc. 23rd Annual IEEE Engineering in Medicine and Biology Society Intl. Conf. pp. 2461-2464.

Gupta, et al., "Despeckling of Medical Ultrasound Images Using Data and Rate Adaptive Lossy Compression," IEEE Trans. Medical Imaging, vol. 24, No. 6, Jun. 2005, pp. 743-754.

Li, et al., "A Novel B-Mode Ultrasound Image Compression Method Based on Beam Forming Data," 1998 Proc. Intl. Conf. IEEE Engineering in Medicine and Biology Society, vol. 20, No. 3, pp. 1274-1276.

Strintzis, et al., "Maximum Likelihood Motion Estimation in Ultrasound Image Sequences," IEEE Signal Processing Letters, vol. 4, No. 6, Jun. 1997, pp. 156-157.

Wegener, Albert et al., "Ultrasound Signal Compression" U.S. Appl. No. 12/477,062, filed Jun. 2, 2000, 72 pages.

| n_exp | n_LSB | m_exp |
|---|---|---|
| 0 | 0 | 0 |
| 2 | 0 | 2 |
| 3 | 0 | 3 |
| 4 | 1 | 3 |
| 5 | 1 | 4 |
| 6 | 1 | 5 |
| 7 | 1 | 6 |
| 8 | 2 | 6 |
| 9 | 2 | 7 |
| 10 | 2 | 8 |
| 11 | 2 | 9 |
| 12 | 3 | 9 |
| 13 | 3 | 10 |
| 14 | 4 | 10 |

Figure 10

| Center Frequency | Frequency Band Indicator | Demux Control $x(i), x(i-j)$ | Inverter Control | Modified Sample |
|---|---|---|---|---|
| DC | 1 | $x(i), x(i-1)$ | on = $-x(i-1)$ | $y(i) = x(i) - x(i-1)$ |
| fs/6 | 2 | $x(i), x(i-3)$ | off | $y(i) = x(i) + x(i-3)$ |
| fs/4 | 3 | $x(i), x(i-2)$ | off | $y(i) = x(i) + x(i-2)$ |
| fs/3 | 4 | $x(i), x(i-3)$ | on = $-x(i-3)$ | $y(i) = x(i) - x(i-3)$ |
| fs/2 | 5 | $x(i), x(i-1)$ | off | $y(i) = x(i) + x(i-1)$ |

871 → Center Frequency
872 → Frequency Band Indicator
873 → Demux Control
874 → Inverter Control
875 → Modified Sample

| Band | Center Freq. | Modified Sample | Example Differences or Sums |
|---|---|---|---|
| 1 | DC | $y(i) = x(i) - x(i-1)$ | $x(i)$: 32767 32702 32508 32186 31737 31163 30465 29648 912<br>$x(i-1)$: 32767 32702 32508 32186 31737 31163 30465 29648<br>DIFF: -65 -194 -322 -449 -574 -707 -781 -935 |
| 2 | $f_s/6$ | $y(i) = x(i) + x(i-3)$ | $x(i)$: 32767 16628 -15890 -32756 -17356 -15140 32722 18071 922<br>$x(i-3)$: --- --- --- 32767 16628 -15890 -32756 -17356<br>SUM: --- --- --- 11 -728 -750 -34 715 |
| 3 | $f_s/4$ | $y(i) = x(i) + x(i-2)$ | $x(i)$: 32767 -389 -32758 1166 32730 -1944 -32684 2719 32619 932<br>$x(i-3)$: --- 32767 -389 -32758 1166 32730 -1944 -32684<br>SUM: --- 9 777 28 -778 46 775 -65 |
| 4 | $f_s/3$ | $y(i) = x(i) - x(i-3)$ | $x(i)$: 32767 -15792 -17546 32703 -13977 -19233 32513 -12107 -20845 942<br>$x(i-3)$: --- --- --- 32767 -15792 -17546 32703 -13977 -19233<br>DIFF: --- --- --- -64 1815 -1687 -190 1870 -1612 |
| 5 | $f_s/2$ | $y(i) = x(i) + x(i-1)$ | $x(i)$: 32767 -32671 32382 -31906 31239 -30392 29364 -28166 26801 952<br>$x(i-3)$: 32767 -32671 32382 -31906 31239 -30392 29364 -28166<br>SUM: 96 -289 476 -667 847 -1028 1198 -1356 |

POST-BEAMFORMING COMPRESSION IN ULTRASOUND SYSTEMS

BACKGROUND OF THE INVENTION

The present invention relates to compression of beamformed samples produced in an ultrasound imaging system by a receive beamformer applied to received ultrasound signal samples, particularly to compressing the beamformed samples of each beam independently and decompressing prior to processing for image formation.

Medical ultrasound systems scan the internal anatomy of a subject by transmitting ultrasound beams from a transducer placed on the subject by a clinician. The ultrasound waves are reflected at interfaces of internal tissues having different acoustic impedances, producing echoes. The transducer receives the echoes and converts them to electrical ultrasound signals. The ultrasound system applies a sequence of processing steps to the ultrasound signals to produce an image or series of images that are displayed at a control console for analysis by the clinician. Images formed based on the strength of the received echo are referred to as B-mode images. In addition, the system can measure the Doppler shifts of the ultrasound signals to produce color images indicating the flow of fluid, such as blood, and perform additional analyses useful for diagnosis.

A conventional medical ultrasound transducer includes an array of piezoelectric elements that transmit ultrasound waves when driven by electrical signals, receive the returning echoes and convert the received echoes to a plurality of analog signals. A plurality of analog to digital converters (ADCs) sample the analog signals, each producing a stream of digital signal samples. Typical digital signal processing of the signal samples includes beamforming, downconversion, B-mode (brightness) processing and/or Doppler processing, scan-conversion and image processing for display. The beamformer applies delay and sum operations to the streams of signal samples to form an array of beamformed samples corresponding to a particular direction in the field of view. The beamformer can produce a number of arrays of beamformed samples corresponding to different directions in the field of view by applying different delay patterns to the streams of signal samples. Depending on the type of diagnostic information desired, B-mode processing and/or Doppler processing are then performed on the beamformed samples to form B-mode detected samples and/or Doppler detected samples. The spatial coordinates of the detected samples still correspond to the beam geometry of the beamformed samples. The scan converter performs coordinate transformations of the detected samples to produce frames of data having a raster format appropriate for display. Additional image processing is applied to the frames of samples to allow their display as two-dimensional (2-D) or three-dimensional (3-D) images.

Current efforts for improving medical ultrasound systems are directed to increasing the diagnostic capabilities of console/cart systems and developing smaller portable devices with improved image quality. For the high-end console or cart systems, it is desirable to increase the number of transducer elements to produce higher resolution and/or 3-D images to expand the diagnostic capability. Increasing the number of transducer elements increases the amount of data communicated from the transducer head to the console processor, which can require a higher bandwidth communication channel and a larger cable connection. The data acquisition capacity of the transducer head is constrained by requirements for manipulation and form factors. Hand-carried and handheld ultrasound devices are economical and desirable for use in small clinics, mobile treatment units and the home. For these devices, battery life is also a constraint. More efficient processing, transfer and storage of ultrasound signal data in the ultrasound system can conserve power, data transfer bandwidth and memory capacity.

Compression of ultrasound signal data can provide benefits for both console/cart systems and portable systems. The benefits include reducing the data transfer bandwidth, memory capacity and power requirements of the system. For a portable or hand-carried ultrasound system, these benefits reduce weight and increase battery life. For a console system, compression mitigates the impact of increasing amounts of data acquired by the transducer head and transport of the data to the ultrasound signal processor. Compression that is computationally efficient introduces the benefits of compression with low or no impact on system complexity.

The present description uses the term "compression" to refer to data compression of ultrasound signal samples where the number of bits representing the signal samples is reduced and the signal samples are later decompressed prior to processing for display. Some descriptions of ultrasound imaging systems use the term compression to mean "pulse compression," not data compression. Pulse compression refers to filtering and/or modulation of the transmitted ultrasound pulses and inverse filtering and/or demodulation of the received ultrasound pulses. (For example, see "Parameter optimization of pulse compression in ultrasound imaging system with coded excitation," by V. Behar and D. Adam in Ultrasonics vol. 42, pp. 1101-1109, 2004.) Some descriptions of ultrasound imaging systems use the term compression to mean "log compression," not data compression. In that context, log compression refers to calculating the logarithm of processed ultrasound data, typically the magnitude detected data prior to display. (For example, see "Signal Processing Overview of Ultrasound Systems for Medical Imaging," by A. Murtaza et al., Texas Instruments SPRAB 12, pp. 1-26, November 2008). Both pulse compression and log compression intentionally change characteristics of the transmitted or received ultrasound signals in the time domain and frequency domain. Data compression of the received ultrasound signal samples followed later by decompression is a process that preserves the signal characteristics in the time and frequency domains. The present description refers to lossless and lossy compression of ultrasound signal samples. In lossless compression, the decompressed samples have identical values to the original samples. In lossy compression, the decompressed samples are similar, but not identical, to the original samples. The present description uses to the term "frame" to refer to an array of ultrasound data, either raw or processed, that is eventually processed to form an ultrasound image for display. Descriptions of ultrasound imaging systems in the art also use the term "screen" to refer to a frame of ultrasound data. In the present description, "real time" means a rate that is at least as fast as the sample rate of a digital signal. The term "real time" can be used to describe rates for processing, transfer and storage of the digital signal. The sample rate is the rate at which an ADC forms samples of a digital signal during conversion of an analog signal. Some descriptions of ultrasound imaging systems in the art use the term "real time" to refer to the frame rate for display of the ultrasound images. The present description relates real time to the sample rate instead of the frame rate interpretation.

Previous applications of data compression in ultrasound systems have included alternatives for data compression before and after scan conversion for image formation. In U.S. Pat. No. 6,315,722 entitled "Ultrasonic Diagnostic Device,"

issued on Nov. 13, 2001, Yaegashi describes a time axis extension unit for storing ultrasound signal samples output from an ADC unit. The time axis extension unit writes the data at the rate output from the ADC unit and reads the data out at a lower rate. The time axis extension unit stores signal samples for one screen, or frame, and can be implemented using first-in first-out (FIFO) memories. A data compression unit compresses signal samples read from the time axis extension unit. Yaegashi describes applying image compression technologies, such methods based on the discrete cosine transform (DCT) for exploiting spatial correlation within one frame of data or MPEG compression methods for multiple frames of data. (MPEG refers to the video data compression standards developed by the Moving Picture Experts Group.) The compressed samples are stored in a mass memory device, such as a hard disk. The data compression reduces the storage capacity needed in the mass memory device. For producing an image, a data expanding unit decompresses the compressed samples retrieved from the mass memory device. Conventional operations, including filtering, logarithmic conversion, detection and digital scan conversion, are applied to the decompressed samples for image formation and display. Yaegashi does not disclose beamforming in the processing sequence.

In the US Patent Publication, publication number 2008/0114246, entitled "Transducer Array Imaging System," Randall et al describe compressing ultrasound digital data using mapping, resampling and/or data windowing before and/or after beamforming. The mapping can include requantizing or clipping signal samples. For example, the number of required bits decreases monotonically with depth so that fewer bits per sample may be assigned based on depth. In some embodiments, signal samples from receive channels extending beyond the transmit and receive apertures may be truncated. For imaging a region of interest (ROI), signal acquisition time may be proportional to depth range, so that data acquired before a minimum sample time and/or after a maximum sample time may be truncated if they do not contribute to the formation of image pixels. In some embodiments, the data may be resampled to fewer samples if the display resolution is less than required for full resolution imaging, thus reducing the number of samples transferred.

In U.S. Pat. No. 6,042,545 entitled "Medical Diagnostic Ultrasound System and Method for Transform Ultrasound Processing," issued Mar. 28, 2000, Hossack et al. describe transform compression techniques for ultrasound data after beamforming. Alternatives for beamforming include analog beamforming prior to the ADC or digital beamforming after the ADC. The beamformer generates in-phase and quadrature (I and Q) samples or, alternatively, radio frequency (RF) samples. Beamformed samples corresponding to a two-dimensional (2-D) frame are filtered and transformed to produce a transform domain representation. The transform domain samples are quantized and/or encoded for compression. The compression may be lossless or lossy. Any transform, such as the DCT or the Discrete Wavelet Transform (DWT), quantization function and encoding function may be applied for compressing the frame of data. For example, JPEG compression includes dividing the frames of data into 2-D blocks of data, transforming using a 2-D DCT on each of the blocks, quantizing the transform domain samples, differentially encoding the DC (zero frequency) transform samples between blocks, and entropy encoding the 2-D blocks of quantized transform domain samples (e.g. Huffman encoding). The JPEG compression algorithms can be configured as lossy or lossless. (JPEG compression refers to the standard image compression methods developed by the Joint Photographic Experts Group.) Additional operations in the transform domain for various image processing functions, such as filtering, are more computationally efficient in the transform domain than the spatial domain. For example, 2-D filtering in the spatial domain uses 2-D convolution operations. In the transform domain 2-D filtering uses more efficient multiplications by the transform domain filter coefficients. The compressed transform domain data can be stored for later image formation. For decompression, the inverse encoding and transform functions are applied prior to processing for display.

In the U.S. Pat. No. 6,855,113, entitled "Diagnostic Information Generation Apparatus and Ultrasonic Diagnostic System," issued Feb. 15, 2005, Amemiya et al. describe compressing frames of ultrasound data prior to wireless transmission from an ultrasonic wave unit to an information unit. The ultrasonic wave unit includes the transducer and a processer for subsequent beamforming, B-mode imaging and Doppler imaging. General purpose data compression standards are applied to the B-mode imaging data or Doppler imaging data, such as JPEG compression for single frame or MPEG compression for multiple frames. The compressed data are transmitted using a standard wireless communication modality to the information unit. The information unit includes a central processing unit (CPU) that decompresses the received data in accordance with the compression standard. The CPU further processes the decompressed B-mode imaging data and decompressed Doppler imaging data for display.

In the PCT published application, international publication number WO 97/09930, entitled "Ultrasonic Diagnostic Apparatus for Compressing and Storing Data in CINE Memory," published Mar. 20, 1997, Lee describes compressing ultrasound data prior to storage in a CINE memory and decompressing data retrieved from the CINE memory. A CINE memory includes several banks organized by time. In this system, the ultrasonic probe performs beamforming prior to the ADC, so the ADC output data represent beamformed samples. Compression is applied to a frame of data and can be applied before or after scan conversion. The Lempel-Ziv-Welch (LZW) algorithm is applied for compression and decompression. The LZW algorithm is based on detecting repeated patterns of bits in the data and assigning codes to the repeated patterns. The compressed data for a frame retrieved from the CINE memory are decompressed and further processed for display.

In the Japanese patent application, publication number 2005-081082, entitled "Ultrasonograph and Ultrasonic Data Compression Method," published Mar. 31, 2005, Akihiro describes three embodiments for compressing ultrasound data after analog beamforming. In the first embodiment, an ADC generates I and Q samples of the analog beamformer output signals. The compressor calculates the differences between the I,Q samples of adjacent beams followed by run-length encoding of the differences to form the compressed data. The compressed data are stored in memory. Compressed data retrieved from memory are decompressed and processed for image display. In the second embodiment, an ADC generates RF samples of the analog beamformer output samples. The compressor calculates differences between the RF samples of adjacent beams followed by run-length encoding. The compressed samples are stored in memory, retrieved, decompressed and processed for image display. In the third embodiment, beamformer output is further processed to generate B-mode image frames and Doppler image frames prior to compression. The compressor calculates frame to frame differences to produce compressed data frames. The compressed data frames are stored in memory, retrieved, decompressed and further processed for display.

In the U.S. Pat. No. 4,751,929, entitled "Ultrasonic Bloodstream Diagnostic Apparatus with Dual Displays of Velocity Profiles and Average Flow Velocity," issued Jun. 21, 1988, Hayakawa et al. describe compressing Doppler frequency detected data. The compressor operates on the output of a squaring and adding circuit that calculates the magnitude squared of the real and imaginary parts of the frequency spectrum samples. The compressor re-encodes the bits of each sample output from the adder to reduce the number of bits in the representation. The compressor operates on the adder output sample to encode the location of the most significant bit in the mantissa, preserve a fixed number of most significant bits and remove the remaining least significant bits. The resulting compressed word for each sample includes the fixed number of most significant bits and a code indicating the number of least significant bits eliminated from the original sample. A variable number of least significant bits are removed from each sample, so the compression is lossy.

In the paper entitled "A Novel B-Mode Ultrasound Image Compression Method Based on Beam Forming Data," 1998 Proc. Intl. Conf. IEEE Engineering in Medicine and Biology Society, Vol. 20 No. 3, pp. 1274-76, Li et al. describe compressing beamformed samples for transmission in a tele-ultrasound system. The DWT is applied to a frame of 128×512 beamformed samples. The coefficients of subimages in the vertical direction are quantized and encoded using arithmetic coding. After decompression, scan conversion is applied to the frame of 128×512 decompressed samples to form the frame of 512×512 samples for display.

Several papers describe different methods for compressing ultrasound images after scan conversion for image formation. A few examples include the following. In the paper entitled "Comparative Survey of Ultrasound Images compression Methods Dedicated to a Tele-Echography Robotic System," 2001 Proc. 23$^{rd}$ Annual IEEE Engineering in Medicine and Biology Society Intl. Conf., pp. 2461-64, Delgorge et al. describe applying different compression methods to ultrasound images. The methods include Fourier transform, DCT, quadtree decomposition, DWT, fractals, histogram thresholding and run length coding. The methods are applied to 512× 512 ultrasound images after scan conversion. In the paper entitled "Despeckling of Medical Ultrasound Images Using Data and Rate Adaptive Lossy Compression," IEEE Trans. Medical Imaging, vol. 24, No. 6, June 2005, pp. 743-54, Gupta et al. describe combining compression with an algorithm to remove speckle from the ultrasound image. The DWT is followed by the speckle removal algorithm, quantization and entropy encoding. In the paper entitled "A Tele-Operated Mobile Ultrasound Scanner Using a Light-Weight Robot," IEEE Trans. Information Technology in Biomedicine, Vol. 9, No. 1, March 2005, pp. 50-58, Delgorge et al. describe applying various lossless and lossy compression methods to ultrasound images. The lossless methods include Huffman, arithmetic coding, Lempel-Ziv, run length coding and Fano coding. The lossy methods include various JPEG versions, including JPEG, JPEG-LS and JPEG2000. In the paper entitled "Maximum Likelihood Motion Estimation in Ultrasound Image Sequences," IEEE Signal Processing Letters, Vol. 4, No. 6, June 1997, pp. 156-7, Strintzis et al. describe applying MPEG compression to a sequence of ultrasound images. The method includes detecting motion vectors for 8×8 blocks of pixels between consecutive frames in the sequence of images. The motion vectors are encoded for frame to frame MPEG compression.

The commonly owned U.S. Pat. No. 7,009,533 (the '533 patent), entitled "Adaptive Compression and Decompression of Bandlimited Signals", dated Mar. 7, 2006, describes algorithms for compression and decompression of certain bandlimited signals. The commonly owned and copending U.S. patent application Ser. No. 12/477,062 (the '062 application), filed Jun. 2, 2000, entitled "Ultrasound Signal Compression," describes compression of ultrasound signal samples output from analog to digital converters and decompression prior to beamforming operations. The present application is directed to compression of the ultrasound beamformed samples resulting from beamforming operations applied to the ultrasound signal samples.

There is a need for efficient data transfer of ultrasound beamformed samples between components of the ultrasound imaging system. There is a need for computationally efficient data compression of ultrasound beamformed samples to improve data transfer with minimal impact on system complexity.

SUMMARY OF THE INVENTION

Embodiments of the present invention have been made in consideration of the foregoing conventional problems. The present invention provides an apparatus and method for compressing the beamformed samples representing one or more beams produced by a receive beamformer in an ultrasound imaging system. The receive beamformer is applied to a plurality of sequences of ultrasound signal samples received during a sampling window to form one or more beams, each represented by an array of beamformed samples. The sequences of ultrasound signal samples are produced by analog to digital conversion of analog ultrasound signals output by the transducer elements during the sampling window. The method and apparatus of the present invention provide for compressing the beams to form compressed beams, including compressing the beamformed samples in the array representing a particular beam to form the compressed beamformed samples of a corresponding compressed beam. The compression of a particular beamformed sample in the array depends in part on a characteristic of at least one other beamformed sample in the array. Each beam is compressed independently of another beam corresponding to the sampling window. The compressed beams are transferred across a digital interface to a signal processor. At the signal processor, the compressed beams are decompressed prior to processing for image formation.

In an embodiment of an apparatus for the present invention, the compressor includes one or more compression units. A corresponding compression unit applies the compression operations to a corresponding beam output from the receive beamformer independently of other beams corresponding to the sampling window. The corresponding compression unit is configured to compress a particular beamformed sample based in part on a characteristic of at least one other beamformed sample of the corresponding beam.

In another aspect of the present invention, the compression operations include applying block floating point encoding to groups of beamformed samples of a particular beam to form groups of compressed beamformed samples. A group multiplexer interleaves the groups corresponding to two or more compressed beams to form a multiplexed sequence for transfer across the digital interface. The compressed groups of the received multiplexed sequence are decompressed to form groups of decompressed beamformed samples. A group demultiplexer rearranges the decompressed groups to restore the original group order for the corresponding decompressed beams. In another embodiment of present invention the compression operations include calculating differences between beamformed samples of a corresponding beam followed by block floating point encoding of the difference samples to form the compressed beam.

The correlation among the beamformed samples within a beam is exploited by compressing a particular beamformed sample depending in part on a characteristic of another beamformed sample in the same beam. For an embodiment including block floating point encoding, the characteristic is the exponent value for the beamformed sample having the maximum magnitude in a group of beamformed samples within the beam. The block floating point encoding represents each beamformed sample in the group based on the exponent value and the value of the beamformed sample itself. For an embodiment including calculating differences between pairs of beamformed samples in the beam, the characteristic is the value of each beamformed sample in the pair. Compressing each beam independently of other beams in the sampling window allows efficient computations and low latency for producing the compressed beams.

An advantage of compressing the beamformed samples in an ultrasound imaging system includes reducing the bandwidth needed for transfer of the compressed beamformed samples over the digital interface to the signal processor. For a system architecture wherein the receive beamformer and compressor are housed in the transducer head, the digital interface may be a wired or a wireless communication link. For a wired communication link, the digital interface may be implemented by a lower cost cable assembly, such as PCIe (Peripheral Component Interconnect Express) cable link or an optical fiber link. For a wireless communication link, the reduced bandwidth required may reduce the cost and complexity of the transmitters and receivers implementing the wireless link. For a system architecture where the bandwidth of the digital interface is fixed, compression of the beamformed samples allows more beams in compressed form to be transferred to the signal processor for image formation. The signal processor may use the greater number of beamformed samples to produce an ultrasound image having improved resolution or a larger field of view.

Another advantage of the present invention includes efficient storage of the compressed beamformed samples. For a system architecture where the beamformed samples are stored in a memory or other storage media, the storage capacity required for storing the compressed beamformed samples is reduced compared to uncompressed beamformed samples.

Another advantage of the present invention includes computationally efficient compression and decompression. The implementations of compression and decompression are less complex, reducing the burden on system resources and reducing the cost. Other aspects and advantages of the present invention can be seen on review of the drawings, the detailed description and the claims, which follow.

BRIEF DESCRIPTION OF THE DRAWINGS

FIG. 10 is a table of exemplary values of n_exp, n_LSB and m_exp.

FIG. 19 shows the operations that produce modified samples 832 based on the center frequency.

FIG. 20 gives the sums or differences of samples x(i) and x(i−j) for the examples of FIG. 17.

DETAILED DESCRIPTION

Figure 1:
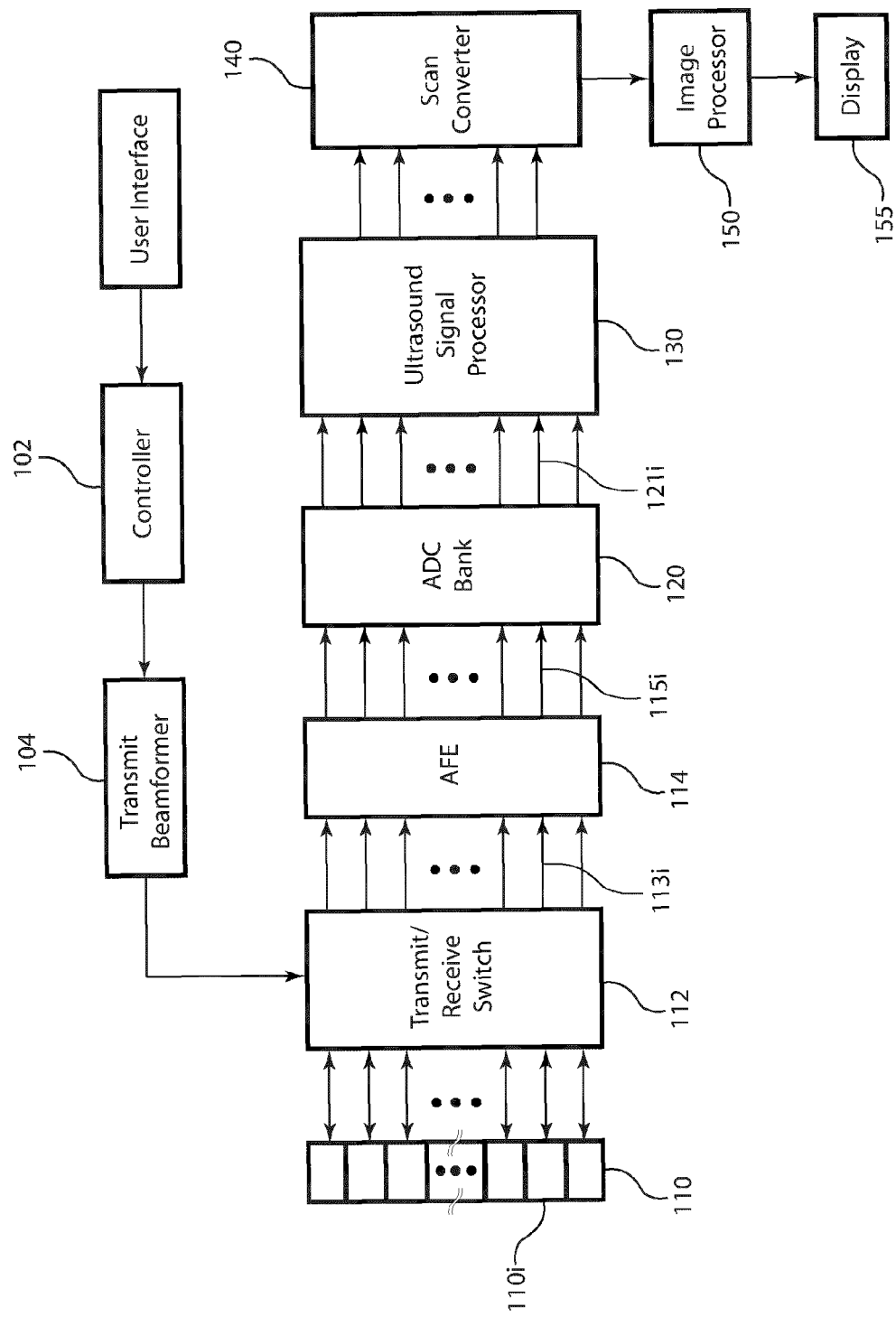
FIG. 1 is a block diagram of an example of a typical medical ultrasound system in accordance with the prior art.

FIG. 1 is a block diagram of an example of a typical medical ultrasound system in accordance with the prior art. The transmit beamformer 104 is of a construction known in the art, such as a digital or analog beamformer. The transmit beamformer 104 generates one or more excitation signals in response to the system controller 102. The excitation signal has an associated center frequency, typically in the 1 to 20 MHz range. The excitation signals from the transmit beamformer 104 are provided to the ultrasound transducer 110 via the transmit/receive switch 112. The ultrasound transducer 110 comprises an array of transducer elements 110i. The ultrasound transducer 110 is of a construction known in the art that enables the coupling the ultrasound waves to the subject being examined. The transducer elements 110i both launch and receive ultrasound waves. The transmit/receive switch 112 includes the switching circuitry for transmit and receive modes. For transmit mode, the transmit/receive switch 112 couples the excitation signals from the transmit beamformer 104 to the transducer 110. For receive mode, the transmit/receive switch 112 couples the received ultrasound signals from the transducer 110 to the analog front end (AFE) 114. For transmission, the transducer elements 110$i$ convert the excitation signals to produce ultrasonic acoustic waveforms. In particular, the transducer 110 converts the excitation signals into ultrasound waveforms that travel in directions within the subject in response to the transmit beamformer 104. Scattering sites having interfaces with different acoustic impedances reflect the ultrasonic waveforms, causing echoes to be returned to the transducer 110. The plurality of transducer elements 110$i$ receives the echoes and converts them to a plurality of analog ultrasound signals. The transmit/receive switch 112 couples the plurality of analog ultrasound signals from the transducer 110 to the AFE 114 during a sampling window. The sampling window corresponds to an interval of time during which the received echoes represent reflections from scattering sites within a desired depth range in the subject. The controller 102 sets the sampling window in accordance with user input or a scan protocol and provides the timing control information to the transmit/receive switch 112. The transmit/receive switch 112 outputs the plurality of analog ultrasound signals in parallel during the sampling window. The AFE 114 amplifies and filters the plurality of analog ultrasound signals in preparation for analog to digital conversion. The AFE 114 can include a low noise amplifier (LNA), a variable gain amplifier (VGA) and a lowpass filter for each analog signal channel 113$i$. The VGA applies a gain profile that increases gain as a function of time, since the received signal strength decreases with time. The decrease in signal strength with time results from the attenuation of the ultrasound wave as it travels a longer path through more tissue. The ADC bank 120 includes a plurality of ADCs to convert the plurality of analog ultrasound signals received during the sampling window to a plurality of sequences of ultrasound signal samples in parallel. The analog ultrasound signal at each ADC input channel 115$i$ is converted to a stream of ultrasound signal samples at the corresponding ADC output channel 121$i$. The ultrasound signal samples have a non-zero center frequency, typically corresponding to the radio frequency (RF) of the received ultrasound signals related to the natural, resonant frequency of the piezoelectric material of the transducer.

Figure 2:
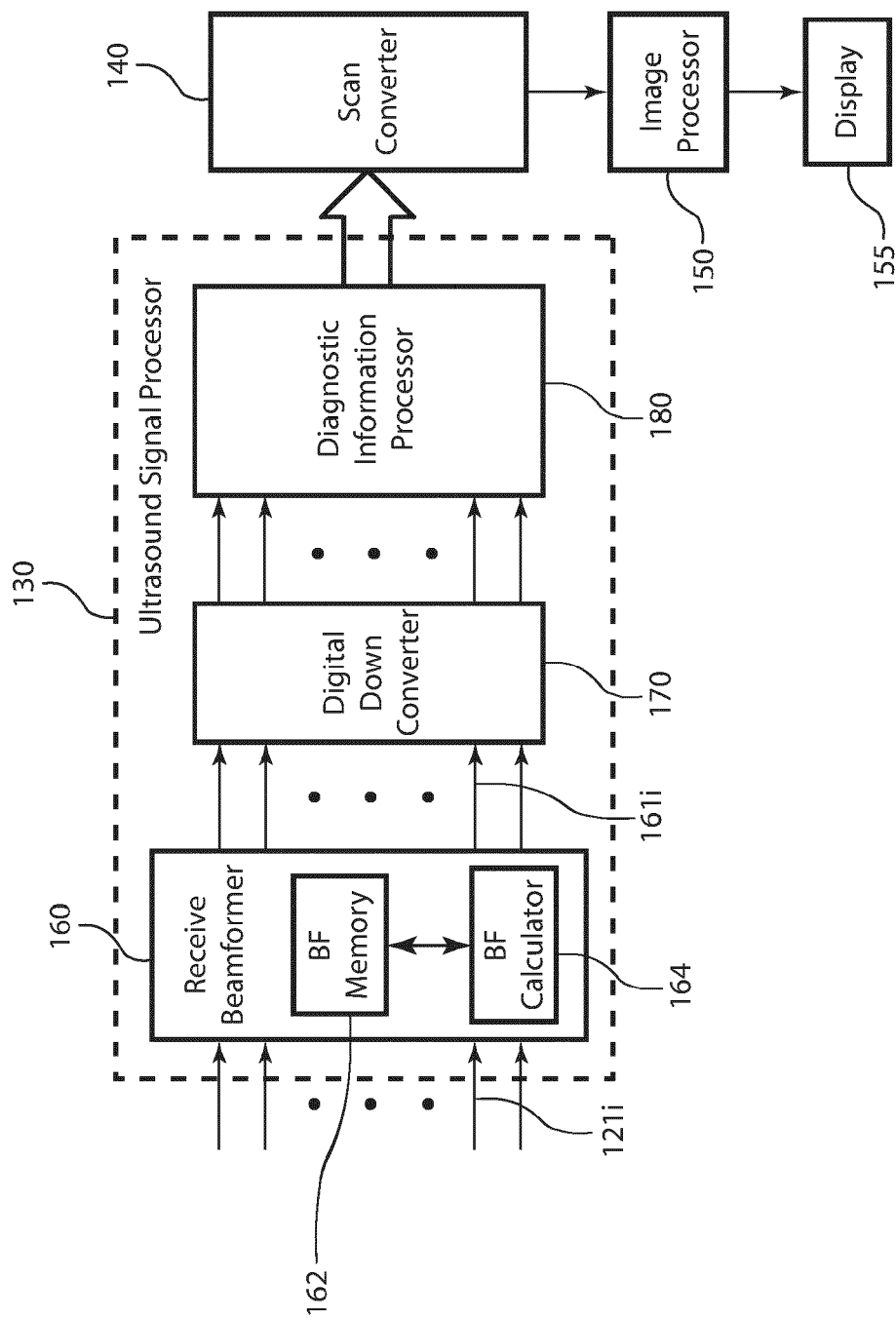
FIG. 2 is a block diagram of the ultrasound signal processor 130, in accordance with the prior art.

The ultrasound signal processor 130 performs the operations that extract the diagnostic information from the ultrasound signal samples, including beamforming, downconversion, B-mode processing and/or Doppler processing, described further with respect to FIG. 2. The ultrasound signal processor 130 can be implemented in one or more processors, such as a digital signal processor (DSP), field-programmable gate array (FPGA), microprocessor or CPU of a computer. The scan converter 140 performs coordinate transformations of a frame of processed samples to produce a frame of ultrasound image samples having a raster (rectilinear) format. The image processor 150 can apply additional image enhancement operations to the ultrasound image samples. The display 160 provides two-dimensional or three-dimensional images for analysis by a user.

FIG. 2 is a block diagram of the ultrasound signal processor 130, in accordance with the prior art. Medical ultrasound systems can perform digital beamforming operations on the RF ultrasound signal samples output from the ADC bank 120. The receive beamformer 160 applies delay, apodization (attenuation) and addition operations to the ultrasound signal samples to form a 1-D array of beamformed samples, or beam, corresponding to a particular direction, or angle, in the field of view. The receive beamformer 160 applies a pattern of delays to the ultrasound signal samples that depends the direction of the beam being calculated. The receive beamformer 160 produces a number of 1-D arrays of beamformed samples corresponding to a number of directions in the field of view. The receive beamformer 160 includes a beamformer (BF) memory 162 to store the ultrasound signal samples for the delay and addition operations of the beamform (BF) calculator 164. The BF calculator 164 can form multiple beams using the ultrasound signal samples retrieved from the BF memory 162 for the same received pulse. The BF calculator 164 can also apply interpolation operations to the ultrasound signal samples to improve the phase resolution of the calculated beams. The receive beamformer 160 can also apply weighting functions to the signal samples prior to the addition operations to implement spatial windowing functions or apodization. The beamformed samples calculated for each angle are provided to a corresponding beamformer output channel 161$i$. The receive beamformer 160 typically has fewer output channels 161$i$ than input channels, comprising the ADC output channels 121$i$. In this configuration, the beamformed samples have an RF center frequency. The digital down converter (DDC) 170 demodulates the beamformed samples to baseband to generate complex baseband I and Q samples for each beam. As an alternative or in addition to the DDC 170, a bandpass filter can be applied to the beamformed samples at a frequency band centered at the desired frequency or the DDC 170 can demodulate the beamformed samples to an intermediate frequency (IF) instead of baseband. Alternative architectures in the art include analog beamforming before analog to digital conversion and digital downconversion of ultrasound signal samples prior to beamforming.

The diagnostic information processor 180 performs the appropriate operations on the I,Q samples for the desired type of ultrasound image. B-mode processing generates information representing the intensity of the echo signal. The magnitudes of the I,Q samples can be calculated to form the detected samples for B-mode imaging. Doppler processing estimates the velocity, variance of velocity and energy from the I,Q samples to form Doppler detected samples. The spatial coordinates of the B-mode detected samples and the Doppler-detected samples correspond to the geometry of the beamformed samples. The scan converter 140 performs coordinate transformations of the detected samples produce frames of data having raster format appropriate for display. The image processor 150 performs additional image processing of the frames of samples prior to display as two-dimensional or three-dimensional images.

Figure 3:
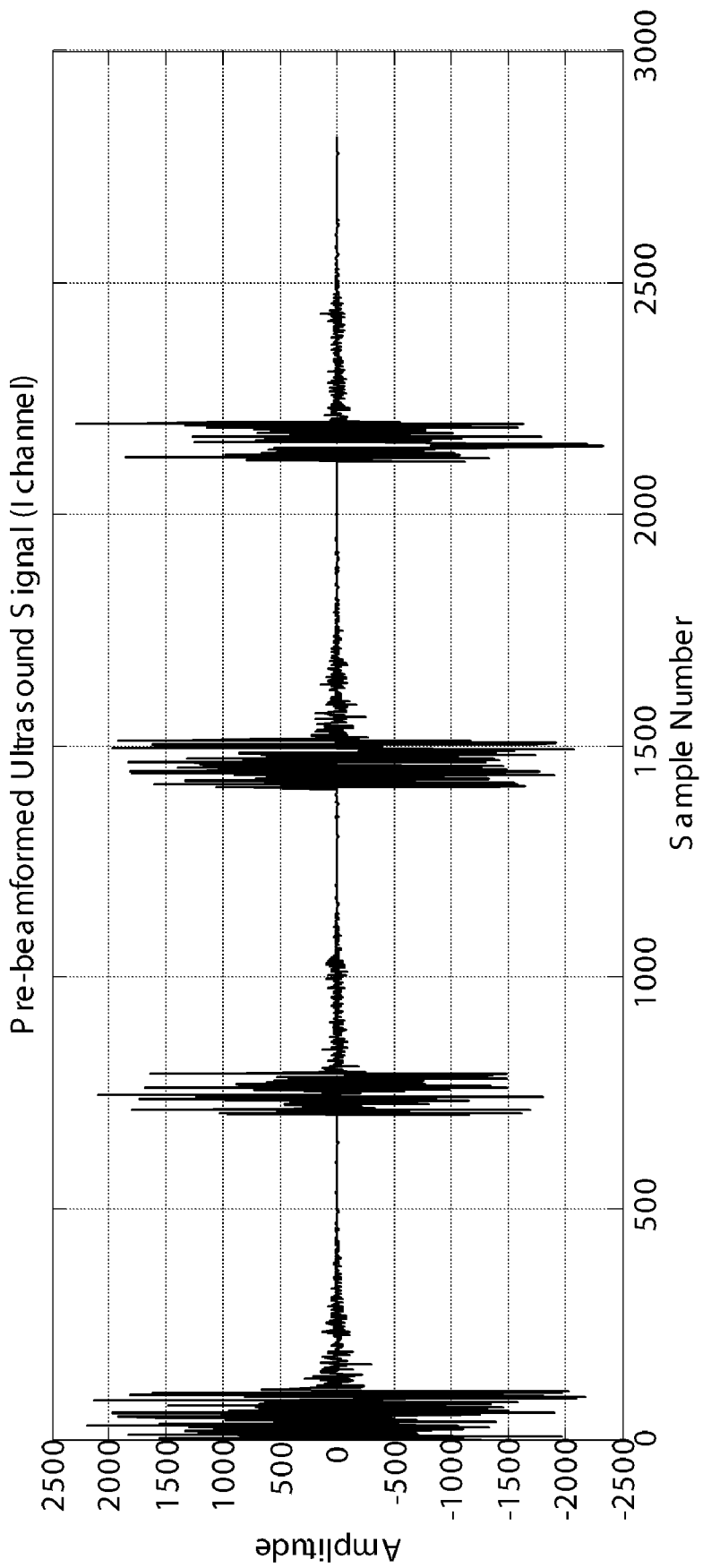
FIG. 3 is a plot of ultrasound signal samples prior to beamforming, in accordance with the prior art.
Figure 4:
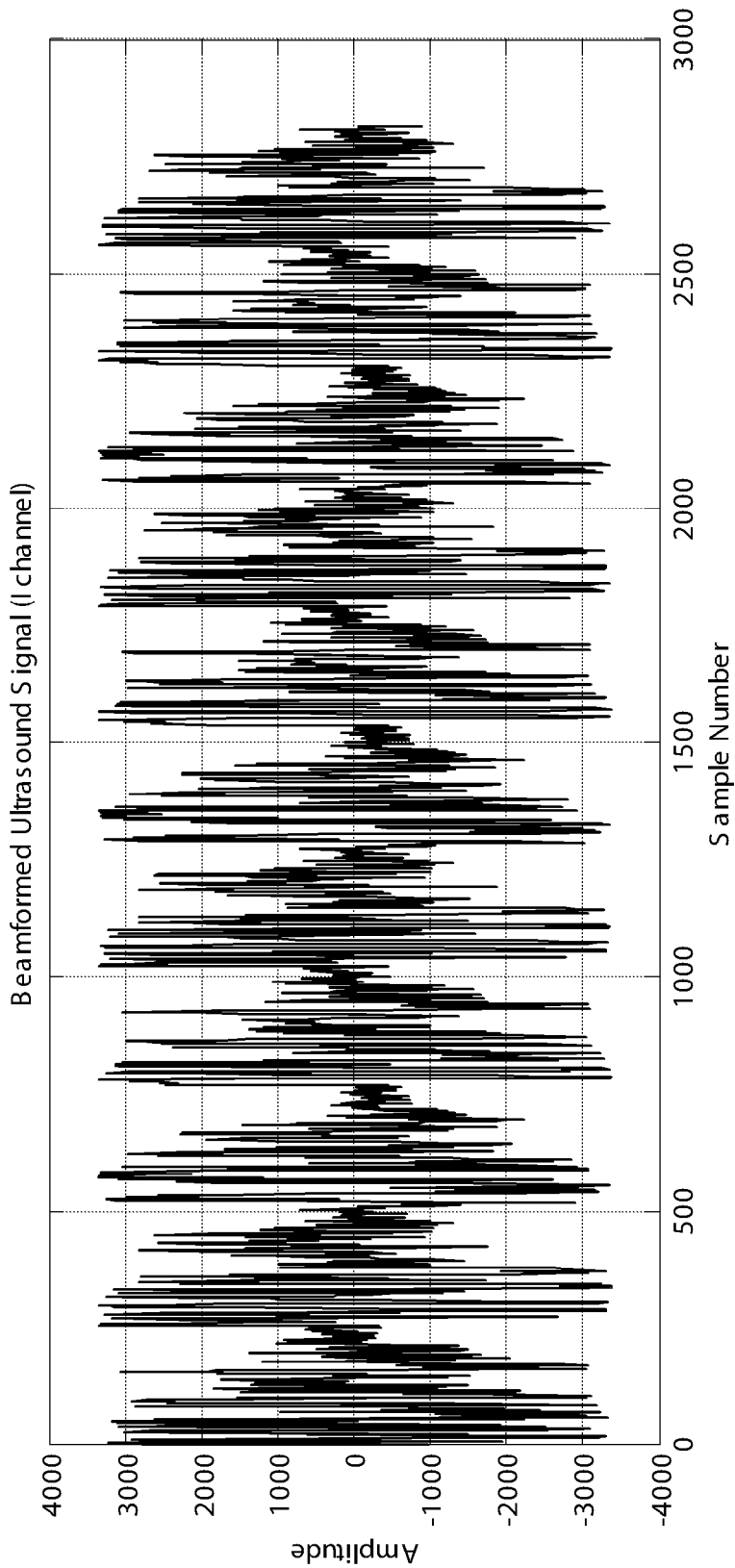
FIG. 4 is a plot of a of the in-phase samples of a beamformed ultrasound signal corresponding to one beamformer output channel, in accordance with the prior art.

FIG. 3 is a plot of ultrasound signal samples prior to beamforming. The plot displays the in-phase samples for four pulse echoes sampled by one ADC of an array of ADCs. For this example, digital down conversion has been applied to the ultrasound signal samples output from the ADC, prior to beamforming, to form the I,Q samples. FIG. 4 is a plot of the in-phase samples of a beamformed ultrasound signal corresponding to one beamformer output channel. For this example, the beamformer combines multiple sequences of I,Q samples output from multiple ADCs by applying delays and weighting functions to the I,Q samples.

Figure 5:
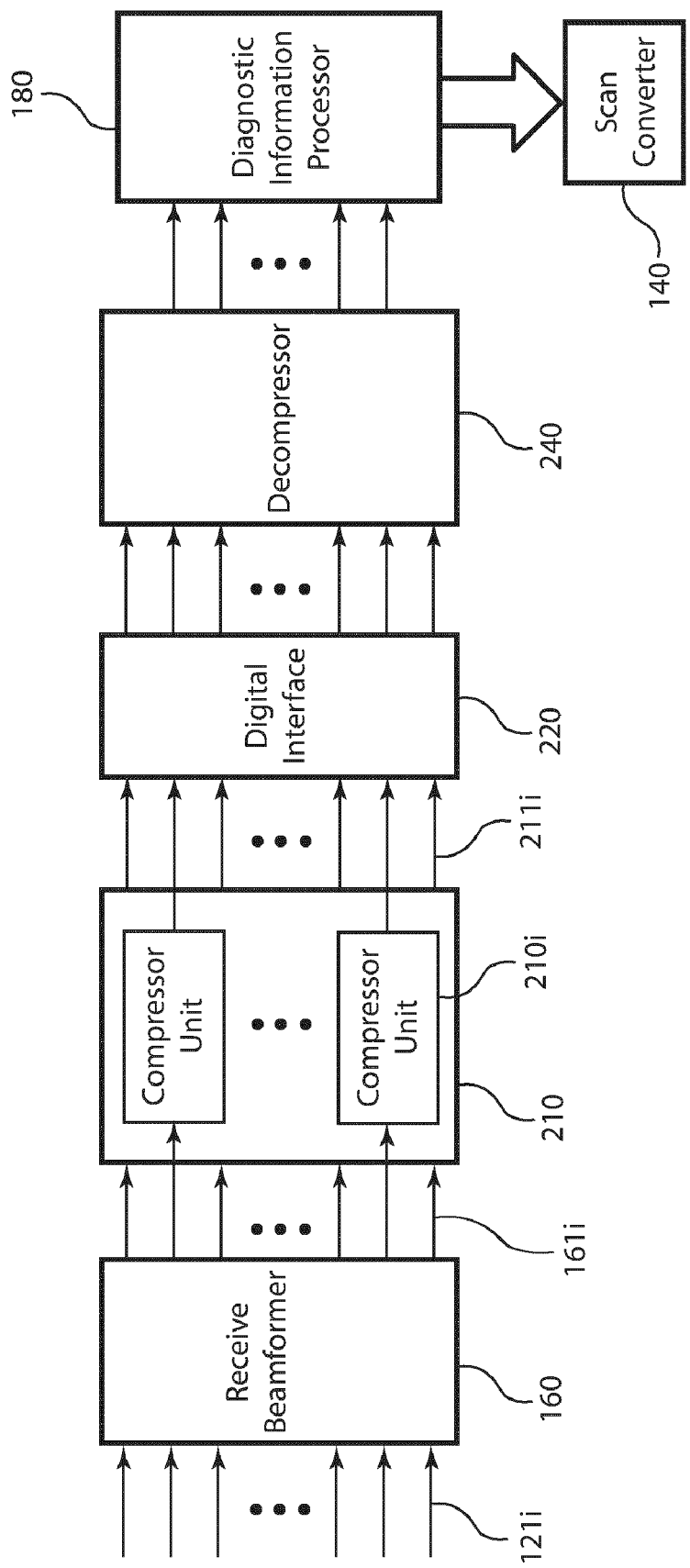
FIG. 5 is a block diagram of an ultrasound imaging system that includes compression of the beamformed samples output from the receive beamformer.

FIG. 5 is a block diagram of an ultrasound imaging system that includes compressing the beamformed samples produced by the receive beamformer 160, in accordance with a preferred embodiment. The compressor 210 includes a plurality of compression units 210$i$, each applying compression operations to a corresponding beamformer output channel 161$i$. The compression unit 210$i$ applies compression operations to the 1-D array of beamformed samples representing a particular beam to produce a corresponding sequence of compressed beamformed samples at the compressor output 211$i$. The beamformed samples of a particular beam are compressed independently of the beamformed samples representing other beams. Alternatively, a compression unit 210$a$ may compress beamformed samples representing multiple beams received from multiple beamformer output channels 161$i$. In this alternative, the compression unit 210$a$ applies the compression operations independently to the beamformed samples representing different beams. The compressed beamformed samples are transferred across a digital interface 220 to the diagnostic information processor 180. The decompressor 240 decompresses the received compressed data to reconstruct the 1-D arrays of beamformed samples for further signal processing operations by the diagnostic information processor 180. The data transfer bandwidth of the digital interface 220 required for transfer of the compressed beamformed samples is reduced compared to the bandwidth required for transfer of uncompressed beamformed samples.

At some point in the processing sequence the processed ultrasound signals are downconverted to an IF or baseband. Downconversion may be applied before or after analog to digital conversion by the ADC bank 120, after beamforming and prior to compression, or after decompression. When downconversion is applied prior to compression, the beamformed samples input to the compressor 210 will have a center frequency at an intermediate frequency (IF) or at zero frequency (baseband). When downconversion is applied after decompression, the beamformed samples input to the compressor 210 will have an RF center frequency. The present description assumes that the beamformed samples are real-valued samples. Alternatively, if the ADCs 120$i$ perform quadrature sampling or if quadrature downconversion applied prior to compression, the beamformed samples will have of I and Q components. In this situation, the compressor 210 will process the I and Q components of the beamformed samples independently.

Figure 6:
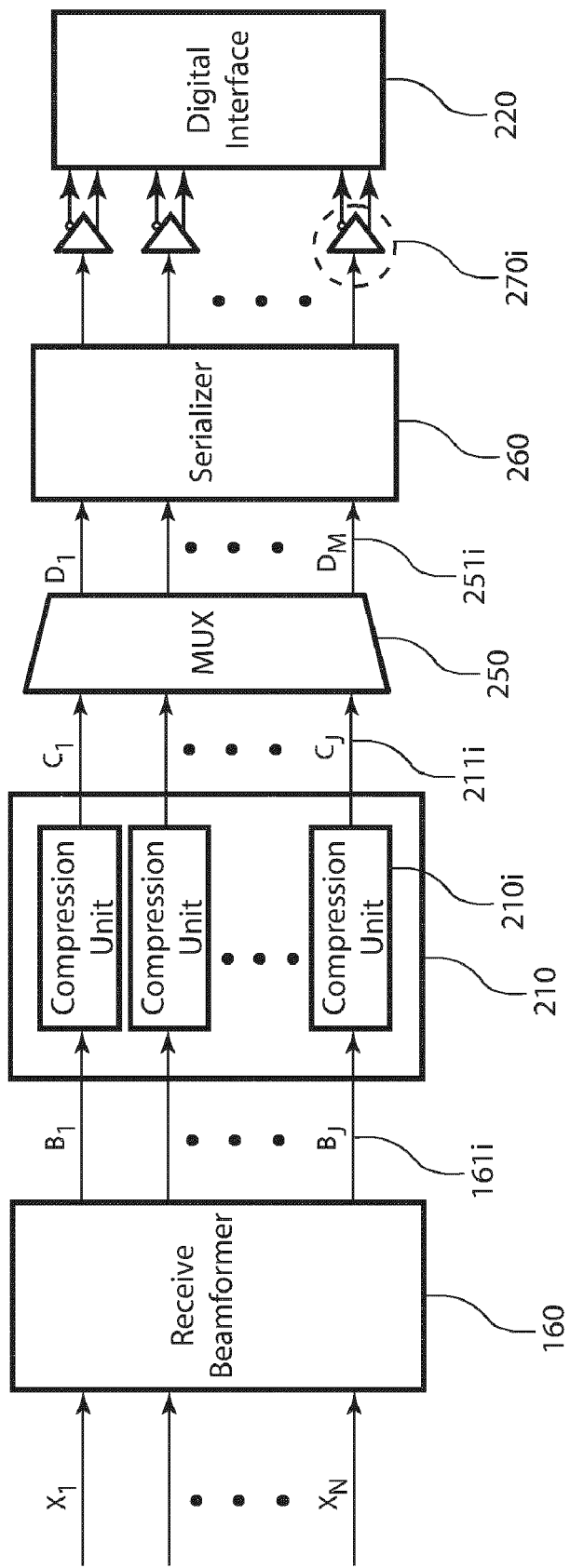
FIG. 6 is a block diagram of an ultrasound imaging system that includes multiplexing the compressed beamformed samples for transfer across fewer data ports.

Since the compressed beamformed samples have fewer bits per sample, the data ports for connecting to the digital interface 220 may have excess bandwidth. The compressed beamformed samples may be multiplexed to form fewer data channels for transfer over the digital interface 220. FIG. 6 is a block diagram of an ultrasound system that includes multiplexing the compressed beamformed samples for transfer across fewer data ports. The receive beamformer 160 receives N streams of ultrasound signal samples, $X_1$ to $X_N$, from the respective ADC outputs 121$i$ and produces J beams, $B_1$ to $B_J$, at the beamformer output channels 161$i$. The compression units 210$i$ produce J corresponding streams of compressed beamformed samples, $C_1$ to $C_J$. The compressed beamformed samples, having a reduced bit rate, are provided to the data ports 270$i$. Preferably, the data ports 270$i$ provide low voltage differential signaling (LVDS) data transmission. Alternatively, the data ports 270$i$ can use serializer-deserializer (SerDes) interfaces for data transmission. The document entitled "LVDS Owner's Manual Including High-Speed CML and Signal Conditioning", Fourth Edition, published in January 2008 by National Semiconductor describes LVDS devices and architectures. The LVDS data transmission has desirable characteristics, including a maximum data transfer rate of 3.125 Gbps, low noise and low power consumption. The differential signaling requires two I/O pins per channel output, one for the positive differential output and one for the negative differential output, referred to as an LVDS pair. The data port 270$i$ has excess bandwidth when the bit rate of the compressed beam at compressor output $C_i$ is lower than the port's maximum data transfer rate. The excess bandwidth can be utilized by combining multiple compressed beams for transfer over a given data port 270$i$. The multiplexer 250 combines J sequences of compressed beamformed samples to form M multiplexed sequences $D_j$, where M<J, for transfer over M data ports 270$i$. The number of compressed beams that can be combined is limited by the bandwidth of the data transfer port 270$i$. The serializer 260 provides the multiplexed sequences of bits to the corresponding data ports 270$i$.

The advantages of multiplexing the compressed beamformed samples to use M data ports include using fewer physical data ports, which in turn reduces the connections and power consumption of the data ports. In applications where the bit rate of the compressed beamformed samples is fixed, the multiplexer 250 has a fixed number of multiplexer outputs 251$i$ for a fixed number of physical data ports 270$i$. Alternatively, a flexible architecture can support a variable number active data ports among the fixed number of physical data ports 270$i$ depending on the bit rate of the compressed beamformed samples. For the flexible architecture, the compressor 210 provides compressed beamformed samples at various bit rates that depend on a user selectable compression ratio parameter. A compression controller (not shown in FIG. 5) provides compression control parameters to the compression units 210$a$ so that the operations produce compressed beamformed samples with a bit rate that corresponds to the desired compression ratio. The compression controller provides multiplexing control parameters to the multiplexer 250 to indicate the number M of multiplexed sequences to produce. The compression controller can also respond to the user input to power down the inactive data ports, thus further conserving power.

The number of compressed beams that can be combined for one data port is limited by the bandwidth of the data port 270$i$. For example, for J=8 beams $B_j$, where each beam has 16 bits per beamformed sample and a sample rate of 50 megasamples per sec. (Msps), the bit rate at each beamformer output channel 161$i$ is 800 Mbps. Suppose the data port 270$i$ has a data transfer rate of up to 800 Mbps and the compressor 210 produces a compression ratio of 2:1. The compressed beam $C_i$ at compressor output 211$i$ has a bit rate of 400 Mbps. In this case, one data port 270$i$ has sufficient bandwidth to transfer 2 compressed beams $C_i$ at the data transfer rate of 800 Mbps. The multiplexer 250 combines the compressed beamformed samples from a set of 2 compressed beams, $C_i$ and $C_{i+1}$, to form a corresponding sequence of multiplexed compressed samples $D_j$ at one multiplexer output 251$i$. In this example, the number of multiplexed sequences provided to the corresponding active data ports is M=J/2=4. The serializer 260 provides sequences of bits to the corresponding data ports 270$i$. After transfer over the digital interface 220, a demultiplexer may receive the M multiplexed sequences and demultiplex them to restore the J compressed beams provided to the decompressor 240. Alternatively, the multiplexer 250 may interleave groups of compressed beamformed samples having a fixed number of samples per group. For this alternative, the decompressor 240 may decompress the groups of compressed beamformed samples prior to demultiplexing, as described below with respect to FIG. 12 and FIG. 13.

The compression methods applied by compression units 210$a$ operate on the beamformed samples of the each beamformer output channel 161$i$ independently of the other beams. The compression methods applied to the beamformed samples depend on the values of other samples within the beam. The compression methods include block floating point encoding and computing first or higher order derivatives of the beamformed samples followed by block floating point encoding. Huffman or other types of encoding can be alternatives to block floating point encoding.

The preferred embodiment of the compression unit 210a applies block floating point encoding to groups of consecutive beamformed samples from the beamformer output channel 161i, each group having N_GROUP samples. The maximum exponent for the N_GROUP samples is encoded and the N_GROUP samples are encoded according to the following steps.

For the first group of N_GROUP samples:
1) Determine the exponent (base 2) for the sample with the maximum magnitude, such as by calculating the $\log_2$ of the maximum magnitude in each group of N_GROUP samples. This indicates the number of bits per encoded sample, or n_exp(0).
2) Absolute encode the exponent n_exp(0) of the first group using S bits, where S is the original number of bits per sample.
3) Encode the N_GROUP samples using n_exp(0) bits per sample.

For the i$^{th}$ group of N_GROUP samples (i>0):
4) Determine the i$^{th}$ exponent (base 2) for the sample with the maximum magnitude, which indicates the number of bits per encoded sample in the i$^{th}$ group, or n_exp(i);
5) Differentially encode the i$^{th}$ exponent by subtracting n_exp(i) from n_exp(i−1) to determine an i$^{th}$ difference value. Encode the i$^{th}$ difference value using a corresponding token, where shorter tokens represent more common difference values and longer tokens represent less common difference values.
6) Encode the i$^{th}$ group of N_GROUP samples using n_exp(i) bits per sample.

For the first group of samples, the exponent n_exp(0) is directly encoded. For example, the exponent n_exp(0) can be encoded as follows, where S is the original number of bits per sample:
  a. 0: n_exp(0)=0 (all 4 sample values are zero)
  b. 1: n_exp(0)=2 (2 bits per sample)
  c. 2: n_exp(0)=3 (3 bits per sample)
  d. etc. until S−1: n_exp(0)=S (S bits per sample)

For the i$^{th}$ group, the exponent n_exp(i) is differentially encoded using a prefix code, where no codeword is the prefix of another codeword. The preferred differential encoding is as follows:
1. Calculate difference: e_diff=n_exp(i)−n_exp(i−1)
2. Encode e_diff as follows:
  a. 0: e_diff=e(i)−e(i−1)
  b. 101: e_diff=+1
  c. 110: e_diff=−1
  d. 1001: e_diff=+2
  e. 1110: e_diff=−2
  f. Etc.

Alternatively, the exponents n_exp(i) may be Huffman encoded instead of differentially encoded.

Figure 7:
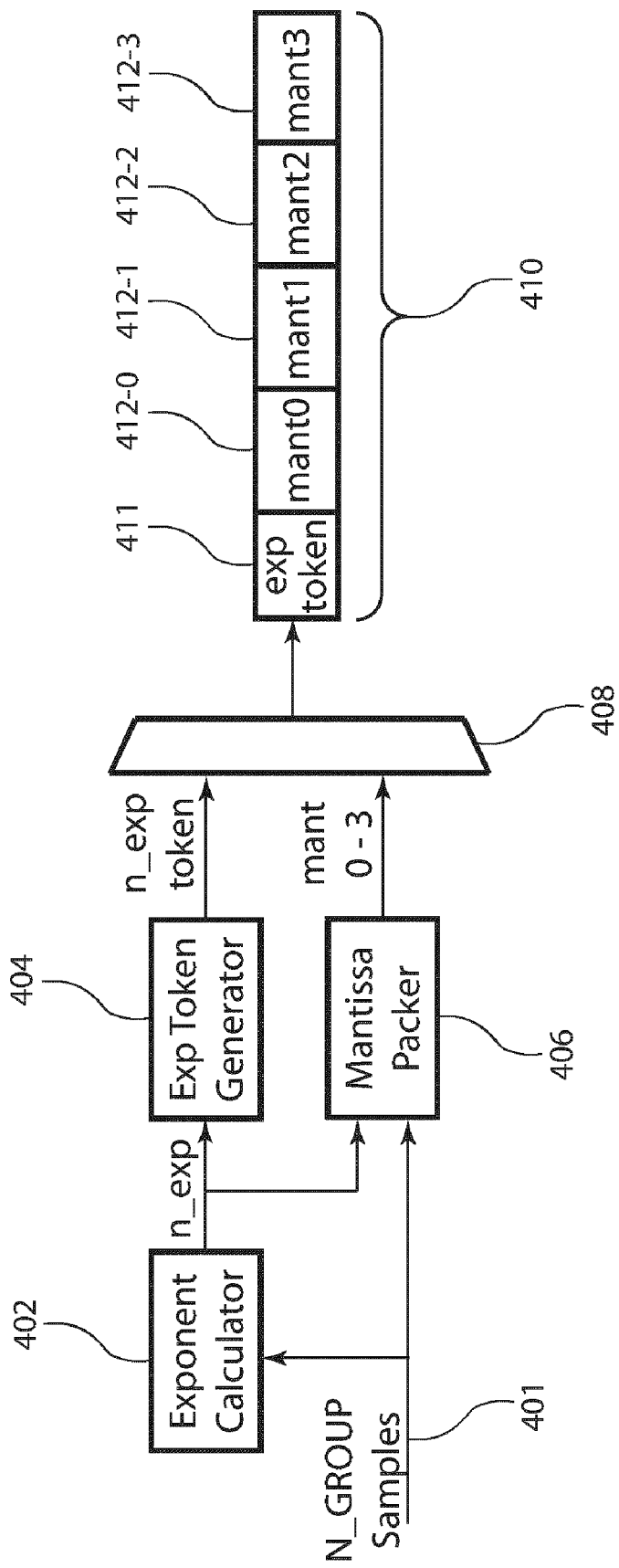
FIG. 7 is a block diagram of the block floating point encoder where N_GROUP=4.
Figure 8:
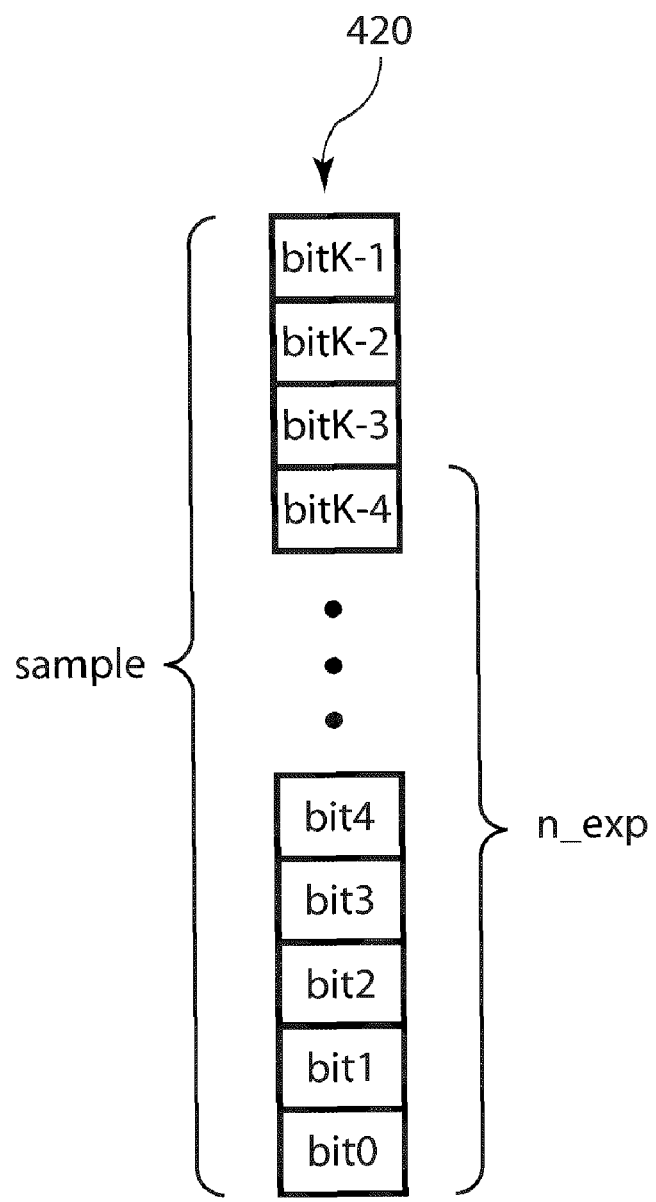
FIG. 8 illustrates an example of selecting n_bits of a sample for encoding.

FIG. 7 is a block diagram of the block floating point encoder where N_GROUP=4. The exponent calculator 402 determines the maximum exponent in bits, n_exp, for the N_GROUP samples as in step 1 and step 4. The exponent token generator 404 encodes the n_exp values as in step 2 and step 5. The mantissa packer 406 encodes the mantissas for the N_GROUP samples as in step 3 and step 6. FIG. 8 illustrates an example of selecting n_bits of a sample for encoding. The input sample 420 is represented by K bits. The n_exp lower bits of the sample 420 are selected for encoding. The sign bit for the sample is appended to the selected bits and the resulting sequence of bits represents the mantissa. Returning to FIG. 7, the multiplexer 408 packs the encoded exponent token 411 followed by the N_GROUP mantissas to form the compressed group 410 representing the N_GROUP compressed samples. For this example, the compressed group 410 includes the exponent token 411 followed by the sequence of four packed mantissas 412-0, 412-1, 412-2 and 412-3. The compression unit 210a concatenates consecutive compressed groups to form the data portion of a compressed packet at the compressor output 211i. The preferred sizes for N_GROUP are three or four samples per group. However, variable group sizes may also be used.

Encoding the mantissas and exponents separately can provide additional compression and mitigate compression error. The difference values of consecutive exponents are calculated and encoded. The exponents vary slowly, so there are relatively few nonzero values separated by strings of zero values. The exponent difference values can be efficiently encoded by representing only the nonzero difference values and their corresponding positions. The position can be represented by the corresponding index value or relative to the position of last nonzero difference value. Encoding of the exponent difference values is lossless, which prevents relatively large errors. For decoding the exponents, the exponent values are reconstructed by integrating the exponent difference values and decoding the corresponding position locations. For decoding of the mantissas, each reconstructed mantissa value is restricted to so that it does not change the value of the corresponding exponent of the decoded sample. For a decoded exponent of n_exp, the reconstructed mantissa can have a maximum value of $2^{n\_exp}-1$. This prevents compression error in the mantissa from changing the value of the exponent.

Figure 9:
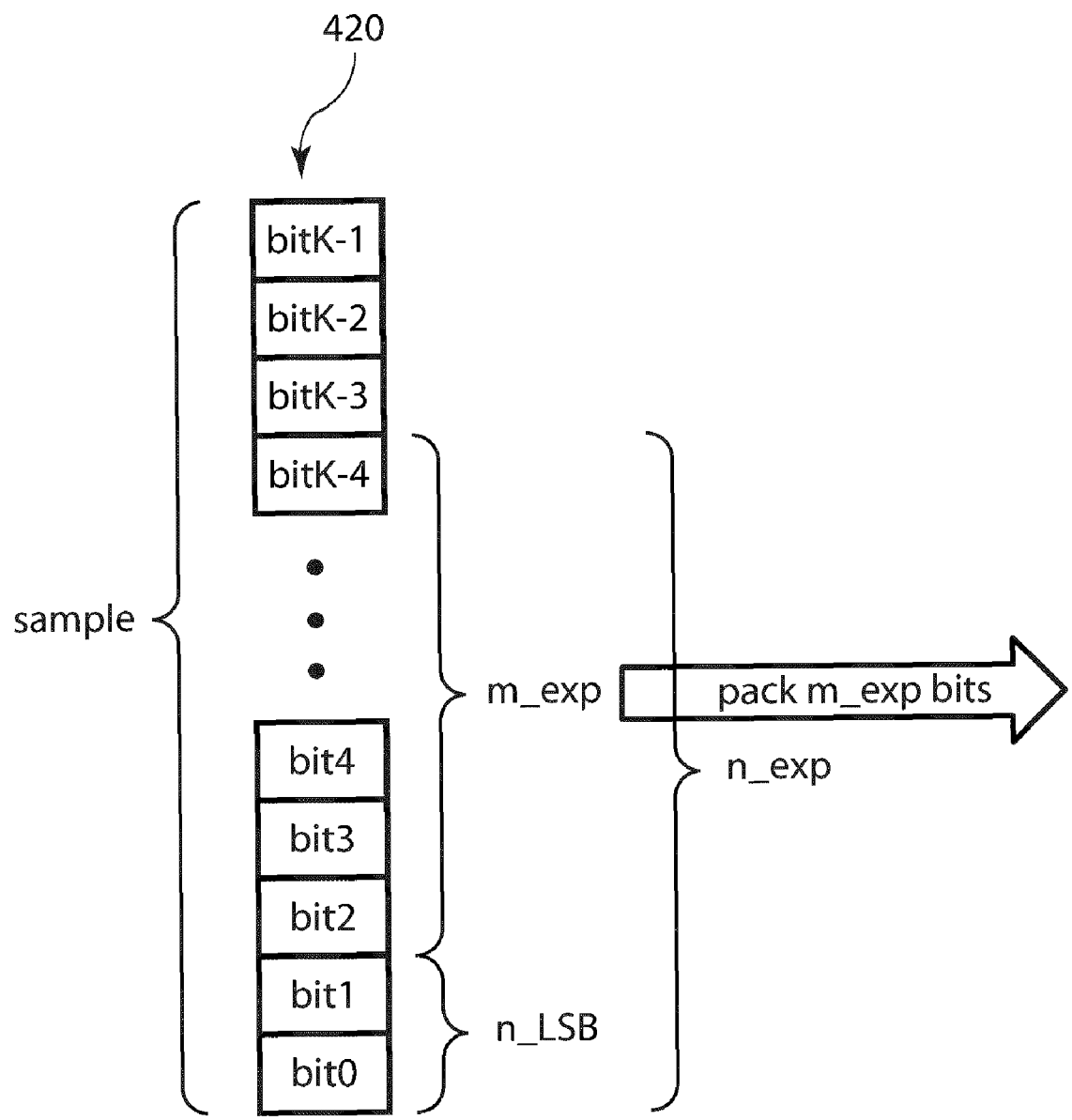
FIG. 9 illustrates an example of selecting bits for representing the reduced mantissa.
Figure 11:
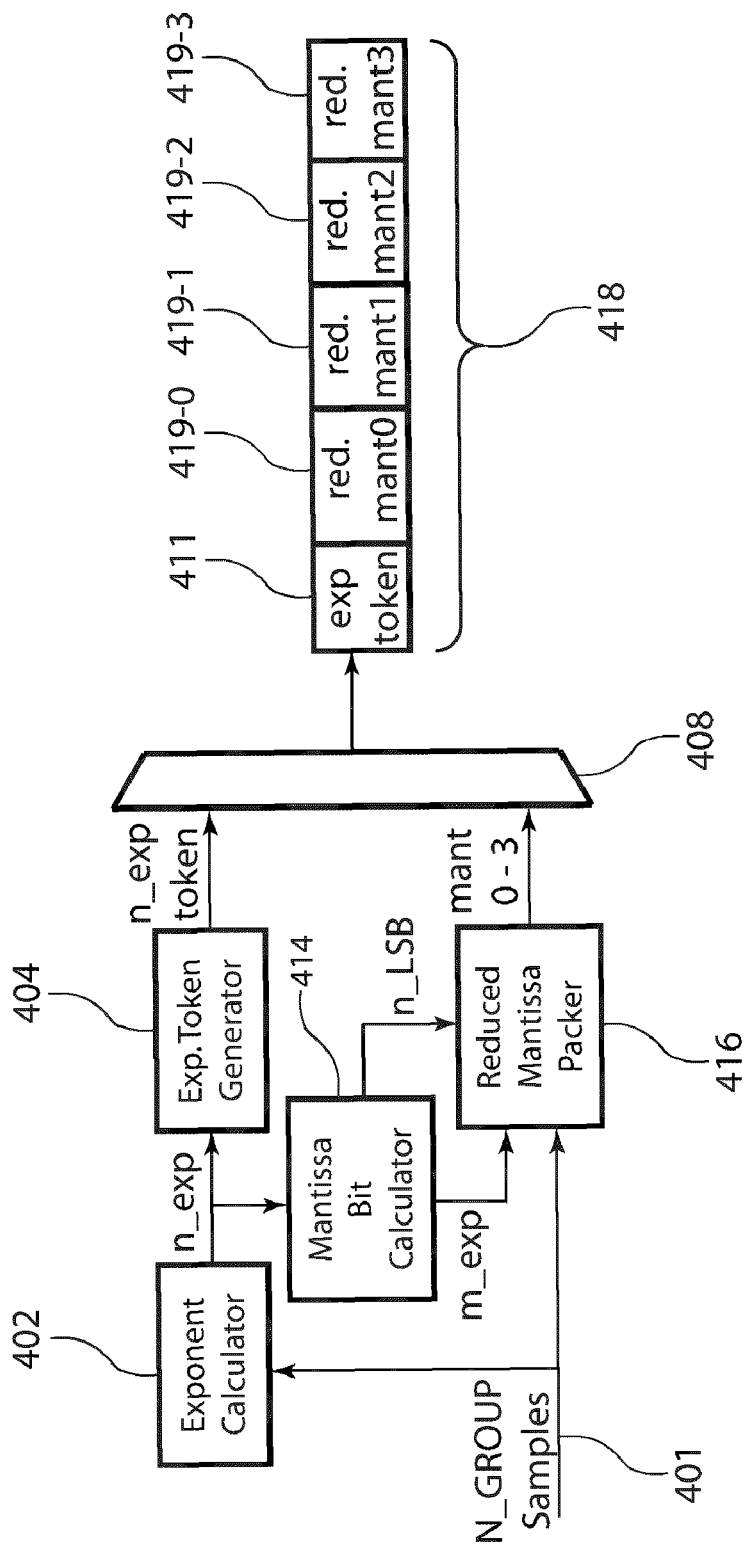
FIG. 11 is a block diagram of block floating point encoding using reduced mantissas.

An alternative block floating point encoding method includes reducing the number of bits representing the mantissa and differential encoding of the exponents as described above. The number of bits representing the mantissas of the N_GROUP samples is reduced by selectively removing a number of least significant bits (LSBs) from each mantissa, depending on the value of n_exp for the group. FIG. 9 illustrates an example of selecting bits for representing the reduced mantissa. The n_exp is determined as in step 1 and step 4 above. Instead of encoding all of the n_exp lower bits of the mantissa, a number n_LSB of bits, starting with the least significant bit, are removed. The remaining m_exp bits (m_exp=n_exp−n_LSB) are selected for encoding. The value of n_LSB depends on the value of n_exp according to a formula or a table. FIG. 10 is a table of exemplary values of n_exp, n_LSB and m_exp. For larger values of n_exp, more LSBs are removed by truncating or rounding to form the reduced mantissa having m_exp bits. For example, if n_exp is 12, 3 LSBs are removed so that 9 mantissa bits are retained for packing the N_GROUP reduced mantissas. The compressor 210 can store a lookup table of values of n_exp, n_LSB and m_exp. Alternatively, the compressor 210 can represent n_LSB and m_exp as a function of n_exp and calculate their values when needed. FIG. 11 is a block diagram of block floating point encoding using reduced mantissas. For the each group of N_GROUP samples, the exponent calculator 402 determines the maximum_exponent n_exp as described above. The mantissa bit calculator 414 determines the number of bits m_exp in the reduced mantissa using a lookup table or formula. The reduced mantissa packer 416 selects the m_exp bits for each of the N_GROUP samples. The multiplexer 408 then packs the exponent token 411 followed by the reduced mantissas 419-0, 419-1, 419-2 and 419-3 to form the compressed group 418. For some conditions, no LSBs are removed from the group of N_GROUP samples. For example, when the magnitude of one or more samples in the N_GROUP samples is less than an acceptable minimum, the N_GROUP mantissas including the original LSBs will be packed. The compressed beams can include compressed groups with or without reduced mantissas.

A compression controller provides compression control parameters to the compression units 210$i$ for block floating point encoding. There can be multiple alternatives lookup tables or formulas for n_LSB, m_exp and n_exp. The compression control parameters include N_GROUP and selection parameters for alternative lookup tables or formulas for n_LSB, m_exp and n_exp. The compression control parameters can be uniform for all the compression units 210$i$. Alternatively, the compression control parameters can have different values for the different compression units 210$i$. The compression controller can respond to user input to select the compression control parameters.

The compressed beamformed samples may be inserted into the data portions of compressed packets for transfer over the digital interface 220. The compressed beamformed samples of a compressed beam corresponding to a sample window may be arranged in one or more compressed packets. Alternatively, sequences of compressed beamformed samples corresponding to multiple compressed beams may be combined to form a compressed packet for transfer over a given data port 270$i$, as described with respect to FIG. 6. The header portion of the compressed packet contains identifying information for the packet. The header can also contain control data that represent the compression control parameters for the compressed beamformed samples in the packet. The information on the compression control parameters can be used by the decompressor 240 to configure the decompression operations.

A preferred embodiment for the multiplexer 250 of FIG. 6 multiplexes groups of N_GROUP compressed beamformed samples. The multiplexer 250 produces M multiplexed sequences by interleaving the compressed groups of the J compressed beams. The J compressed beams are divided into M sets of compressed beams. For each set, the multiplexer 250 interleaves the compressed groups of those compressed beams in the set to form a corresponding multiplexed sequence $D_m$. The multiplexed sequence $D_m$ is a sequence of compressed groups from the corresponding set arranged in a group order by the multiplexer 250. The multiplexer 250 may be implemented as M parallel multiplexers, each receiving the compressed beams of a corresponding set.

Figure 12:
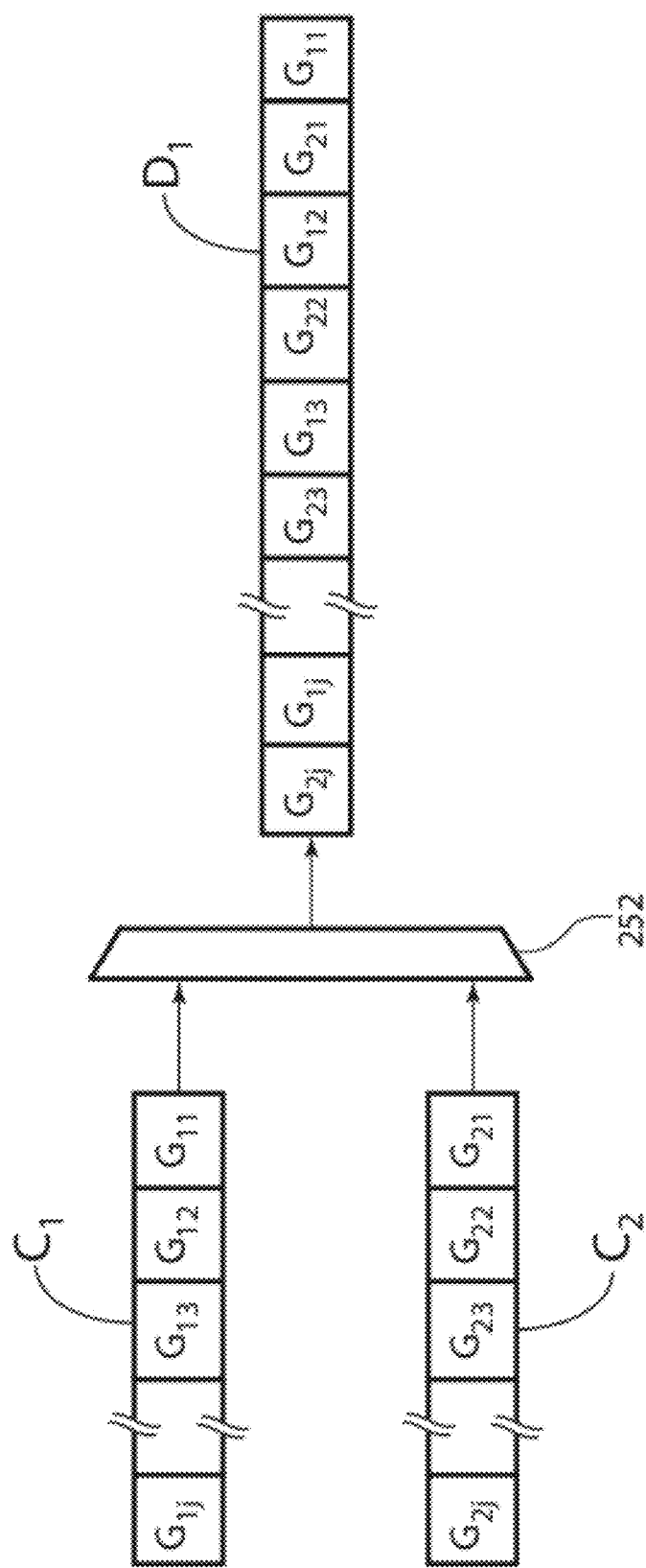
FIG. 12 illustrates an example of multiplexing the compressed groups of a set of compressed beams.

FIG. 12 illustrates an example of multiplexing the compressed groups of a set of compressed beams $C_1$ and $C_2$. The group multiplexer 252 interleaves the compressed groups $G_{1j}$ from the compressed beam $C_1$ and compressed groups $G_{2j}$ from the compressed beam $C_2$ to form the multiplexed sequence $D_1$. In this example, the group order of the multiplexed sequence $D_1$ alternates between compressed beams to form a sequence $G_{1j}$, $G_{2j}$, $G_{1(j+1)}$, $G_{2(j+1)}$, etc. A compressed group $G_{ij}$ may represent the packed bits corresponding to the block floating point compressed group 410 of FIG. 7, the compressed group 418 of FIG. 11 or a compressed group resulting from another encoding method, such as Huffman encoding. The compressed groups have the same number of compressed beamformed samples per group, i.e. N_GROUP samples. However, the number of bits per compressed group may vary since the number of bits per compressed sample may vary. For the block floating point encoding methods described above, the number of bits per compressed group depends on the value of n_exp.

For decompression, the decompressor 240 decodes and unpacks the compressed beamformed samples of the compressed groups corresponding to each compressed beam. For each group of N_GROUP compressed beamformed samples, the decompressor 240 decodes the exponent token to determine the value of n_exp. The differentially encoded exponents are integrated to form the value of n_exp. The N_GROUP mantissas are then reconstructed by unpacking the bits for each mantissa from the compressed group 410 or 418 and mapping the bits to the respective decompressed beamformed samples to form the decompressed group. The decompressed beamformed samples can be represented by the original number of bits per beamformed sample or a different number of bits per beamformed sample depending on the downstream processing requirements. For the block floating point encoder using reduced mantissas, the decompressor 240 also includes a lookup table or formula for determining the values n_LSB based on the decoded values of n_exp. The unpacked bits for the reduced mantissa are appended by n_LSB bits, which can be zeros or dithered values, to approximate the original beamformed sample value. The sequence of decompressed groups calculated from a particular compressed beam form a corresponding decompressed beam.

Figure 13:
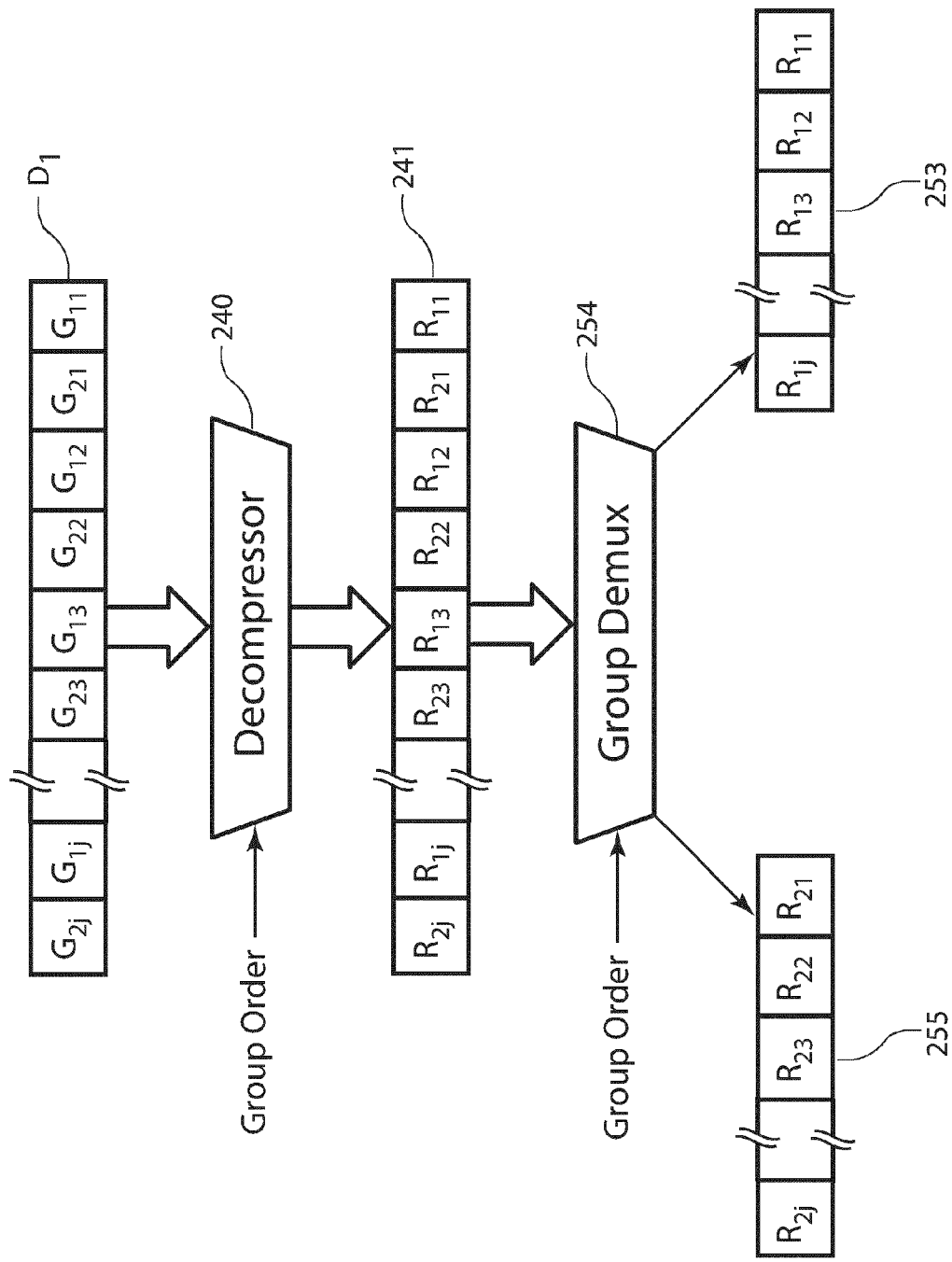
FIG. 13 illustrates an example of demultiplexing corresponding to the multiplexing example of FIG. 12.

For decompression of a multiplexed sequence of compressed groups, the decompressor 240 may be applied to the multiplexed sequence prior to demultiplexing. Referring to FIG. 13, each compressed group $G_{ij}$ the multiplexed sequence $D_1$ includes the exponent token which provides the necessary information for decompressing the N_GROUP compressed beamformed samples of that group. For a differentially encoded exponent token, the decompressor uses the group order of the multiplexed sequence $D_1$ to select exponent tokens corresponding to the same compressed beam for integration to determine the corresponding values of n_exp. The group order may be a fixed parameter for multiplexing and demultiplexing, in which case it is known to the decompressor 240 and the group demultiplexer 254. Alternatively, the group order maybe an adjustable parameter, in which case it can be included in the header portion of the compressed packet along with the other compression parameters. As stated previously, the compressed groups may have different numbers of bits. However, once the groups are decompressed, the N_GROUP decompressed beamformed samples for each group will have the same number of bits per sample. The group order of the decompressed groups is the same as that of the compressed groups. The group demultiplexer 254 reorders the decompressed groups to their original order to form a set of decompressed beams, each having decompressed beamformed samples in the original consecutive order.

FIG. 13 illustrates an example of demultiplexing corresponding to the multiplexing example of FIG. 12. The decompressor 240 applies block floating point decoding to the multiplexed sequence $D_1$ to form a sequence of decompressed groups 241. The decompressed beamformed samples in each group $R_{ij}$ have the same number of bits per sample. The group demultiplexer 254 restores the original order to the groups of decompressed beamformed samples to form the set of decompressed beams 253 and 255. The group demultiplexer 254 uses the group order, i.e. $R_{1j}$, $R_{2j}$, $R_{1(j+1)}$, $R_{2(j+2)}$, etc., to separate the groups of decompressed beamformed samples to their respective decompressed beams 253 and 255. Since the number of samples per group is N_GROUP, the group demultiplexer 254 appends the N_GROUP decompressed beamformed samples of each group $R_{ij}$ to the corresponding decompressed beam.

Alternative methods for compression and decompression of the beamformed samples include performing computations on the beamformed samples within each beam prior to produce modified samples that have lower amplitudes, and therefore need fewer bits to represent them. The '533 patent describes algorithms for compression and decompression of certain bandlimited signals. Some of the alternative compression methods described below are modifications of the algorithms of the '533 patent for beamformed samples.

An alternative method for compression of beamformed samples includes calculating differences between the beamformed samples in each beam independently of the other beams followed by encoding. Calculating first or higher order differences of the beamformed samples can result in difference samples having smaller magnitudes than the original beamformed samples. Encoding the difference samples can result in greater compression than encoding the beamformed samples themselves.

Figure 14:
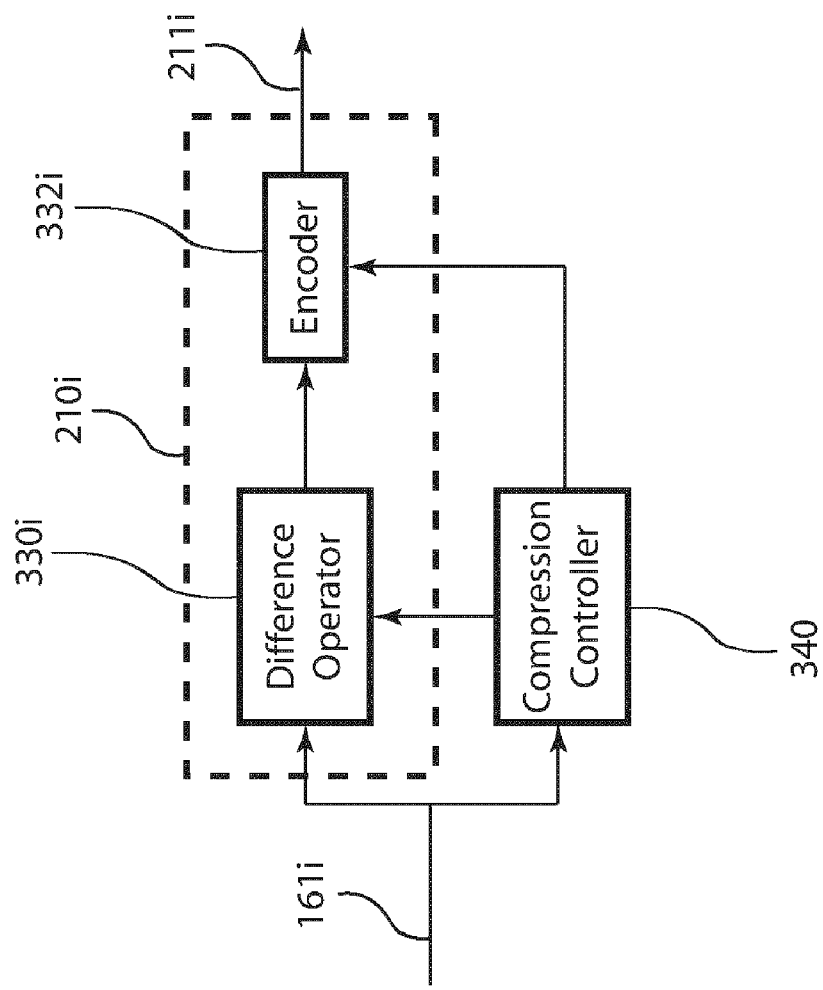
FIG. 14 shows a block diagram of a compression unit that includes differencing operations.

FIG. 14 shows a block diagram of the compression unit 210$i$ that includes differencing operations. The compression unit 210$a$ receives beamformed samples from the beamformer output channel 161$i$. The compression controller 340 provides compression control parameters for the difference operator 330$i$ and encoder 332$i$ of each compression unit 210$i$. The compression control parameters for the difference operator 330$i$ can select first, second or higher order differences. The difference operator 330$i$ applies the selected differencing order to produce the difference samples. The compression control parameter can also select bypassing the difference operations so that the encoder 332$i$ encodes beamformed samples instead of the difference samples. The encoder 332$i$ may apply block floating point encoding of the difference samples, as described above. In this case, the difference samples are provided to the input 401 of the block floating point encoder of FIGS. 7 or FIG. 11. Alternatively, the encoder 332$i$ may apply Huffman encoding or other encoding to the difference samples. The compression control parameter for the encoder 332$i$ can indicate parameters for the block floating point encoder, as described above, or parameters for a Huffman encoder or another encoder. The compression control parameters can be the same or different for the different compression units 210$i$.

The compressor outputs 211$i$ corresponding to different compressed beams may be multiplexed to fewer output channels prior to transfer over the digital interface 220, as described above with respect to FIG. 6 and FIG. 12. The encoder 332$i$ can apply block floating point encoding to the difference samples to produce the compressed groups $G_{ij}$ in FIG. 12 representing the groups of N_GROUP encoded difference samples that comprise the compressed beams $C_1$ and $C_2$. Alternatively, the encoder 332$i$ can apply Huffman encoding to the difference samples so that $G_{ij}$ represents groups of Huffman encoded difference samples having N_GROUP compressed beamformed samples per compressed group. The group multiplexer 252 combines the compressed groups of the compressed beams $C_1$ and $C_2$ to form the multiplexed sequence $D_1$.

Figure 15:
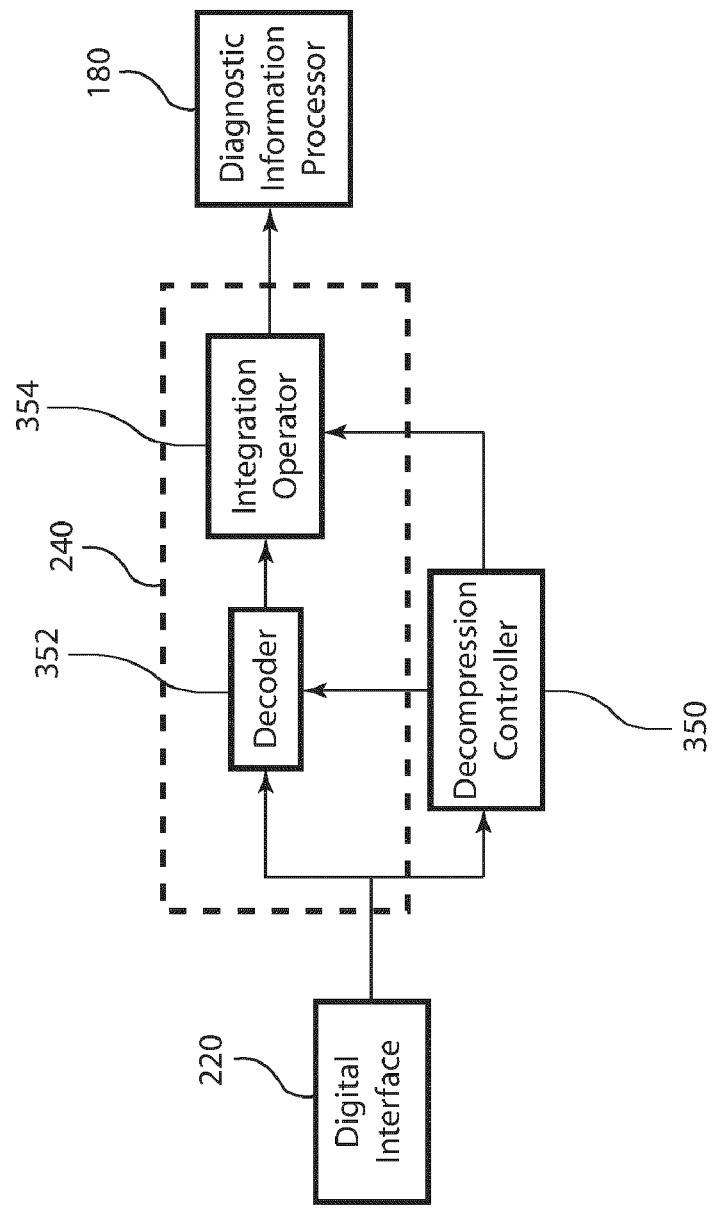
FIG. 15 is a block diagram of decompression operations corresponding to the compression operations described with respect to FIG. 14.

FIG. 15 is a block diagram of decompression operations corresponding to the compression operations described with respect to FIG. 14. The decompressor 240 receives compressed beams from the digital interface 220. The decoder 352 inverts the operations of the encoder 332$i$ to form decoded difference samples. For example, the decoder 352 performs block floating point decoding, Huffman decoding or other decoding. The integration operator 354 adds the decoded difference samples to invert the first or higher order differencing performed for compression to form the decompressed beam provided to the diagnostic information processor 180. If differencing was not performed for compression, the integration operator 354 would be bypassed. The decompression controller 350 provides control parameters to the decoder 352 and integration operator 354. The decompression controller 350 can extract control data from the header of the compressed data packet to determine the control parameters for decompression operations.

The decompressor 240 of FIG. 15 may be applied to a multiplexed sequence of compressed groups of difference samples prior to demultiplexing, as described with respect to FIG. 13. In this case, the decoder 352 decodes the compressed groups $G_{ij}$ in the multiplexed sequence to form groups of decoded difference samples in the group order. For block floating point decoding, if the exponent tokens were differentially encoded, the decoder 352 uses the group order to integrate the exponent tokens corresponding to the same beam to determine the values of n_exp for the corresponding groups. The integration operator 354 uses the group order and n_exp to determine the groups of decoded difference samples corresponding to the same beam. The integration operator 354 integrates the respective groups decoded difference samples to form the decompressed groups $R_{ij}$ of the sequence of 241. The group demultiplexer 254 then separates the decompressed groups $R_{ij}$ into the respective decompressed beams 253 and 255.

Figure 16:
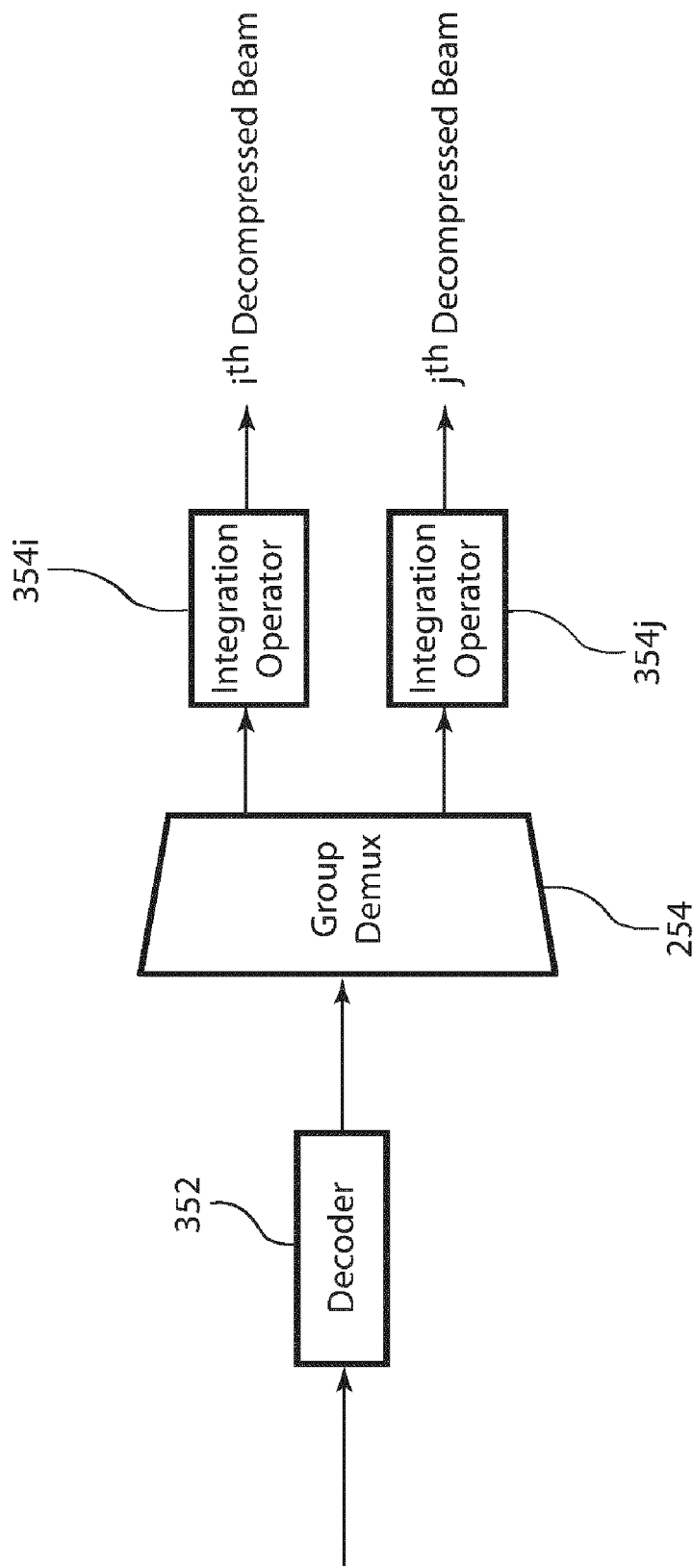
FIG. 16 is a block diagram of demultiplexing the groups of decoded difference samples.

Alternatively, the groups of decoded difference samples may be demultiplexed prior to integration, as shown in FIG. 16. The decoder 352 receives the multiplexed sequence, such as represented by $D_1$ in FIG. 12. The decoder 352 inverts the operations of the encoder 332$i$ to unpack and decode the compressed groups to form groups of decoded difference samples in the group order. For block floating point decoding where the exponent tokens are differentially encoded, the decoder 352 uses the group order to integrate the exponent tokens corresponding to the same beam. The groups of decoded difference samples have the same number of bits per sample and are in the group order corresponding to the multiplexed sequence of compressed groups. The group demultiplexer 254 separates the groups of decoded difference samples to form an array of decoded difference samples corresponding to each beam. The order of decoded difference samples in each array correspond to the order of difference samples output from the difference operator 330$i$. The integration operators 354$i$ and 354$j$ perform the first or higher order integrations of the respective arrays of decoded difference samples to form the $i^{th}$ and $j^{th}$ decompressed beams.

Figure 17:
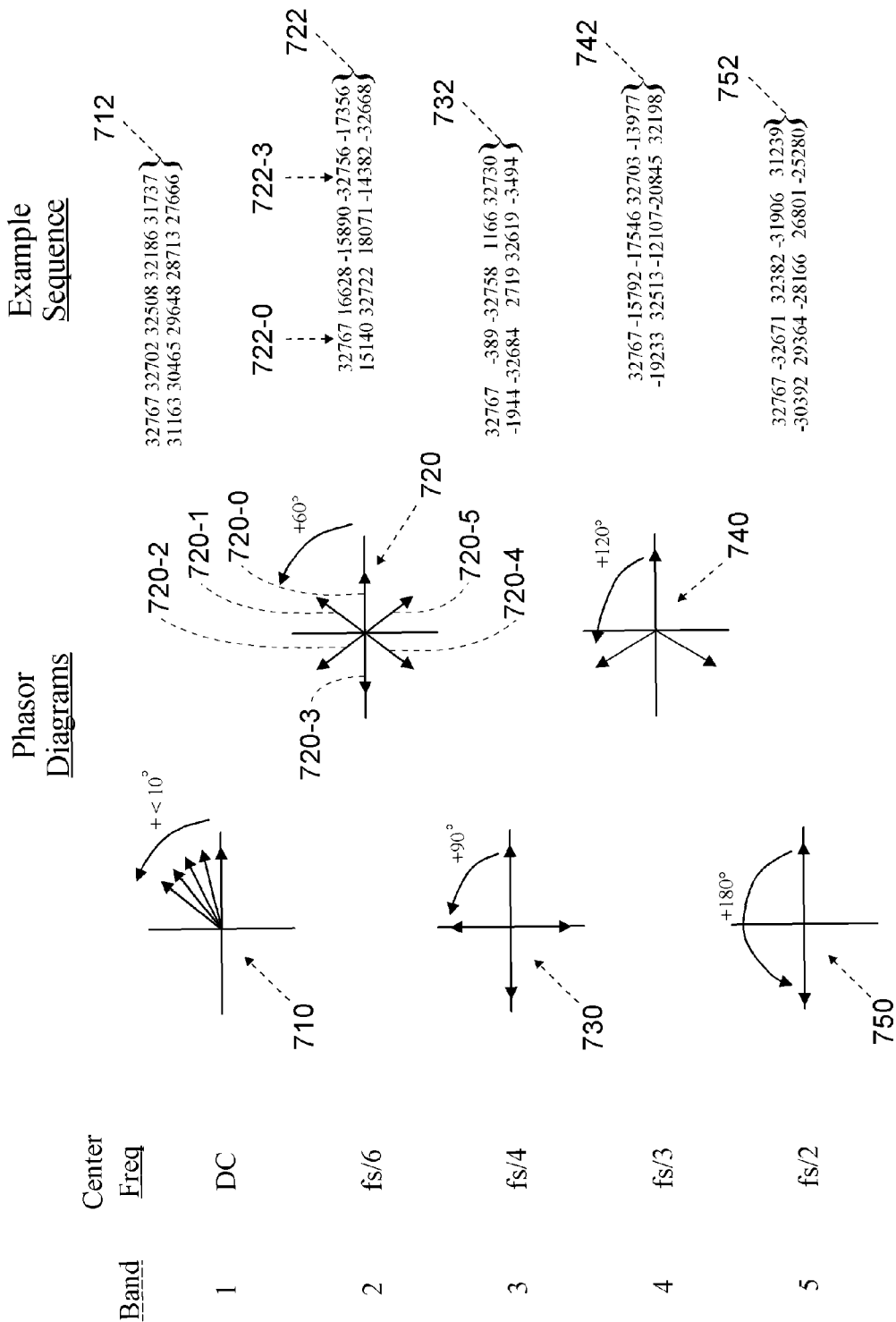
FIG. 17 gives examples that illustrate principles underlying alternatives for compressing beamformed samples with different center frequencies.

Another alternative for compression applies arithmetic operations to the beamformed samples based on the center frequency and sample rate for producing samples having lower amplitudes. FIG. 17 gives examples that illustrate principles underlying alternatives for compressing beamformed samples with different center frequencies. Beginning with the example of a baseband signal, corresponding to row labeled "Band 1" in FIG. 17, the center frequency is near DC (0 Hz) and the phase increase between consecutive samples is less than 10 degrees. The first phasor diagram 710 shows that since the phase changes between consecutive samples are small, the magnitudes of the differences of consecutive samples will be relatively small compared to the magnitudes of the samples themselves. The first example sequence 712 corresponds to samples of a Band 1 baseband signal. Since the differences between consecutive samples are small relative to the sample magnitudes, calculating first or higher order differences, or differential encoding, creates difference samples with smaller data widths than the original samples. Compression using differential encoding described with respect to FIG. 14 is effective for the baseband (Band 1) example. In ultrasound systems where the ultrasound signal samples or the beamformed samples are downconverted to baseband, the compression units 210i can apply differential encoding.

FIG. 17 also gives examples of sampled signals where the center frequency is above DC, but below the Nyquist frequency, $f_s/2$ For Band 2, the center frequency is near $f_s/6$ and the phase increase between consecutive samples is about 60 degrees. The second phasor diagram 720 shows that pairs of samples separated by 180 degrees, or three sample intervals, have similar magnitudes but opposite polarities, as illustrated by pairs of samples (720-0, 720-3), (720-1, 720-4) and (720-2, 720-5). Inverting one of the samples in the pair [or multiplying by (−1)] provides a close estimate of the other sample in the pair. The second example sequence 722 also shows that samples separated by three sample intervals have similar magnitudes and opposite signs. For example, the value of sample 722-0 is 32767 and the value of sample 722-3 is −32756. For Band 2, operations on pairs of samples separated by three sample intervals produce modified samples with smaller data widths. The operation of adding the samples in the pair together produces modified samples having smaller data widths that can be encoded more efficiently.

For the example of Band 3 in FIG. 17, the center frequency is near $f_s/4$ and the phase increase between consecutive samples is about 90 degrees. The third phasor diagram 730 shows that samples separated by 180 degrees, or 2 sample intervals, have similar magnitude and opposite polarity. The third example sequence 732 also shows that every other sample has similar magnitudes and opposite polarities. For Band 3, adding together every other sample will result in modified samples with smaller data widths that can be encoded more efficiently than the original samples.

For the example of Band 4 in FIG. 17, the center frequency is near $f_s/3$ and the phase increase between consecutive samples is about 120 degrees. The fourth phasor diagram 740 shows that samples separated by 360 degrees, or 3 sample intervals, will have similar magnitudes. The fourth example sequence 742 shows that every third sample has similar magnitudes. In this case, forming a difference between samples separated by 3 sample intervals will give a modified sample with a smaller data width that can be encoded more efficiently than the original samples.

For the example of Band 5 in FIG. 17, the center frequency is $f_s/2$ and the phase increase between consecutive samples is about 180 degrees. The fifth phasor diagram 750 shows that samples separated by 180 degrees, or one sample interval, will have similar magnitudes but opposite polarities. The fifth example sequence 752 shows consecutive samples have similar magnitudes and opposite polarities. In this case, adding two consecutive samples will form a modified sample with a smaller data width that can be encoded more efficiently than the original samples.

The above examples described for FIG. 17 show that magnitude reduction can be achieved by performing operations such as addition (or inversion followed by subtraction) or subtraction (or inversion followed by addition) on beamformed samples that are separated by 1, 2 or 3 sample intervals, depending on the ratio of the sample rate to the center frequency. The resulting modified samples are then encoded to form compressed samples. Similar operations can be applied to samples that are separated by four or more sample intervals, depending on the ratio of the center frequency to the sample rate, to produce modified samples with smaller data widths than the original samples.

Figure 18:
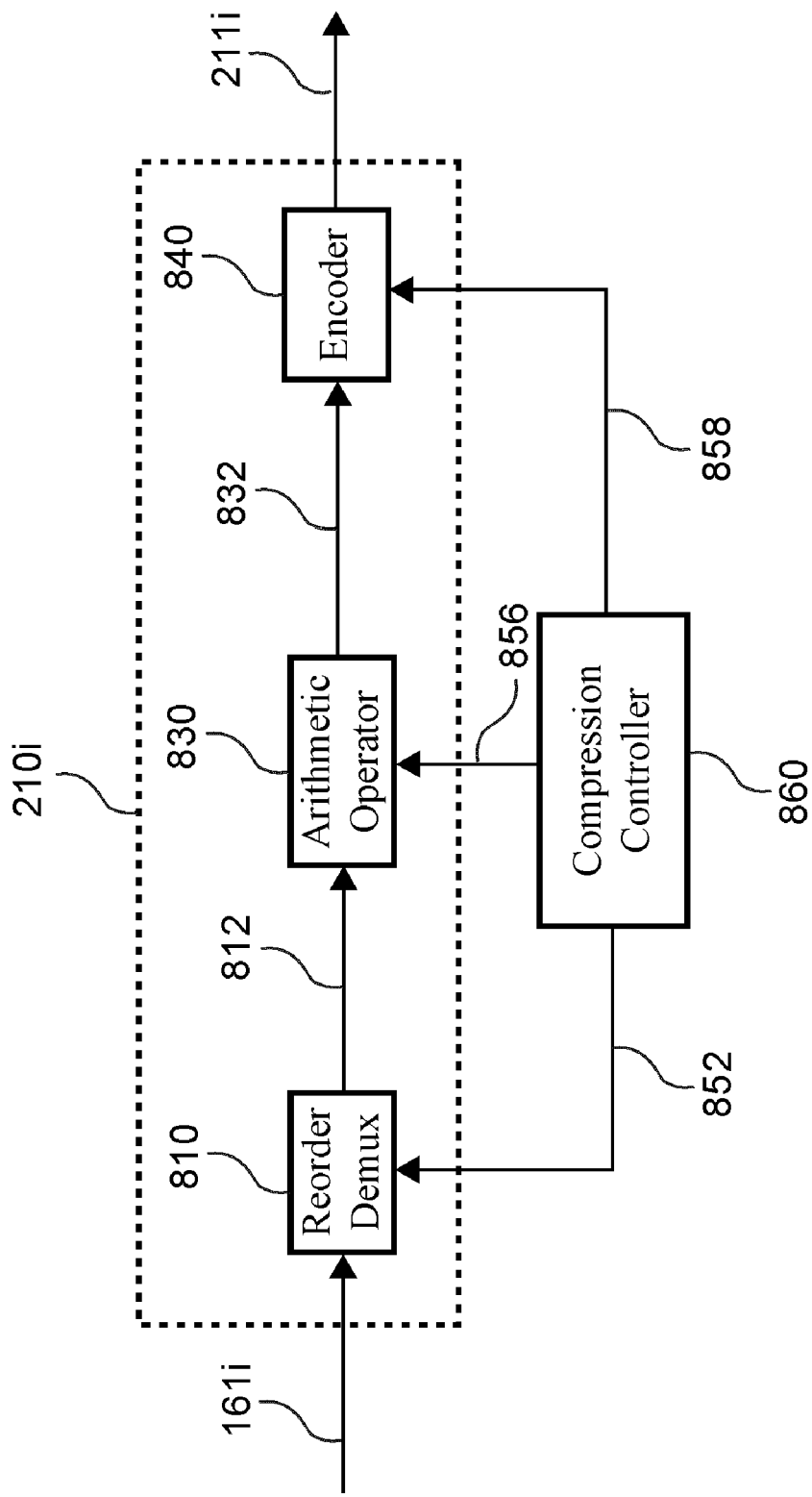
FIG. 18 is a block diagram of the compression algorithm based on the center frequency of the beamformed samples.

FIG. 18 is a block diagram of the compression algorithm based on the center frequency of the beamformed samples. The beamformer output channel 161i corresponding to a particular beam is input to the reorder demux 810. The reorder demux 810 selects beamformed samples so that selected samples are separated by the appropriate number of sample intervals according to compression control parameter 852 to form demultiplexer output 812. Arithmetic operator 830 performs addition or subtraction operations on pairs of demultiplexer output samples 812 according to compression control parameter 856 to form modified samples 832. Arithmetic operator 830 can also be configured to perform higher order differences on the demultiplexer output samples 812. The encoder 840 encodes the modified samples 832 to form compressed beamformed samples. The encoder 840 applies block floating point encoding, Huffman encoding or other encoding to form the compressed samples. For block floating point encoding described with respect to FIGS. 7 and 11, the modified samples 832 are provided to the input 401 of the block floating point encoder.

The compression controller 860 provides control parameters to the compressor elements based on the ratio of the sample rate to the center frequency of the beamformed samples. The reorder demux 810 and arithmetic operator 830 respond to the compression control parameters 852 and 856, respectively, to perform the appropriate operations. FIG. 19 shows the operations that produce modified samples 832 based on the center frequency. The first column 871 gives the possible center frequencies for this example. The second column 872 gives a corresponding frequency band indicator for each center frequency. The indicators can be used as parameters for compression controls 852 and 856. The third column 873 gives the different separations of samples x(i) and x(i−j) at reorder demux output 812 that would be produced in accordance with compression control parameter 852. The fourth column 874 shows the result of selecting the arithmetic operations of addition or subtraction in accordance with compression control parameter 856. When the inverter is "on" the delayed sample, x(i−j) is subtracted. The fifth column 875 shows the mathematical results of the arithmetic operator 830 that produce the modified samples 832, or y(i). The compression controller 860 also provides control of the encoder 840. The compression control parameter 858 can indicate a parameter for block floating point encoding, Huffman encoding or other encoding technique.

FIG. 20 gives the sums or differences of samples x(i) and x(i−j) for the examples of FIG. 17 calculated as described with respect to of FIG. 18 and FIG. 19 for different center frequencies. The example sequences of samples are the same as those of FIG. 17. The samples in the DIFF rows in example sequences 912 and 942 and the SUM rows in example sequences 922, 932 and 952 have substantially lower magnitudes than the corresponding samples, or x(i). The DIFF samples and the SUM samples are examples of modified samples 932 that are input to encoder 840 in FIG. 18.

The compressed beam produced by the encoder 840 at compressor output 211i in FIG. 18 may be multiplexed with other compressed beams to form fewer output channels prior to transfer over the digital interface 220, as described above with respect to FIG. 6 and FIG. 12. The encoder 840 may apply block floating point encoding to the modified samples so that compressed groups $G_{ij}$ in FIG. 12 represent groups of N_GROUP encoded modified samples to form the compressed beams $C_1$ and $C_2$. Alternatively, the encoder 840 may apply Huffman encoding to the modified samples so that $G_{ij}$ represents compressed groups having N_GROUP Huffman encoded modified samples per group. The group multiplexer 252 combines the compressed groups of the compressed beams $C_1$ and $C_2$ to form the multiplexed sequence $D_1$.

Figure 21:
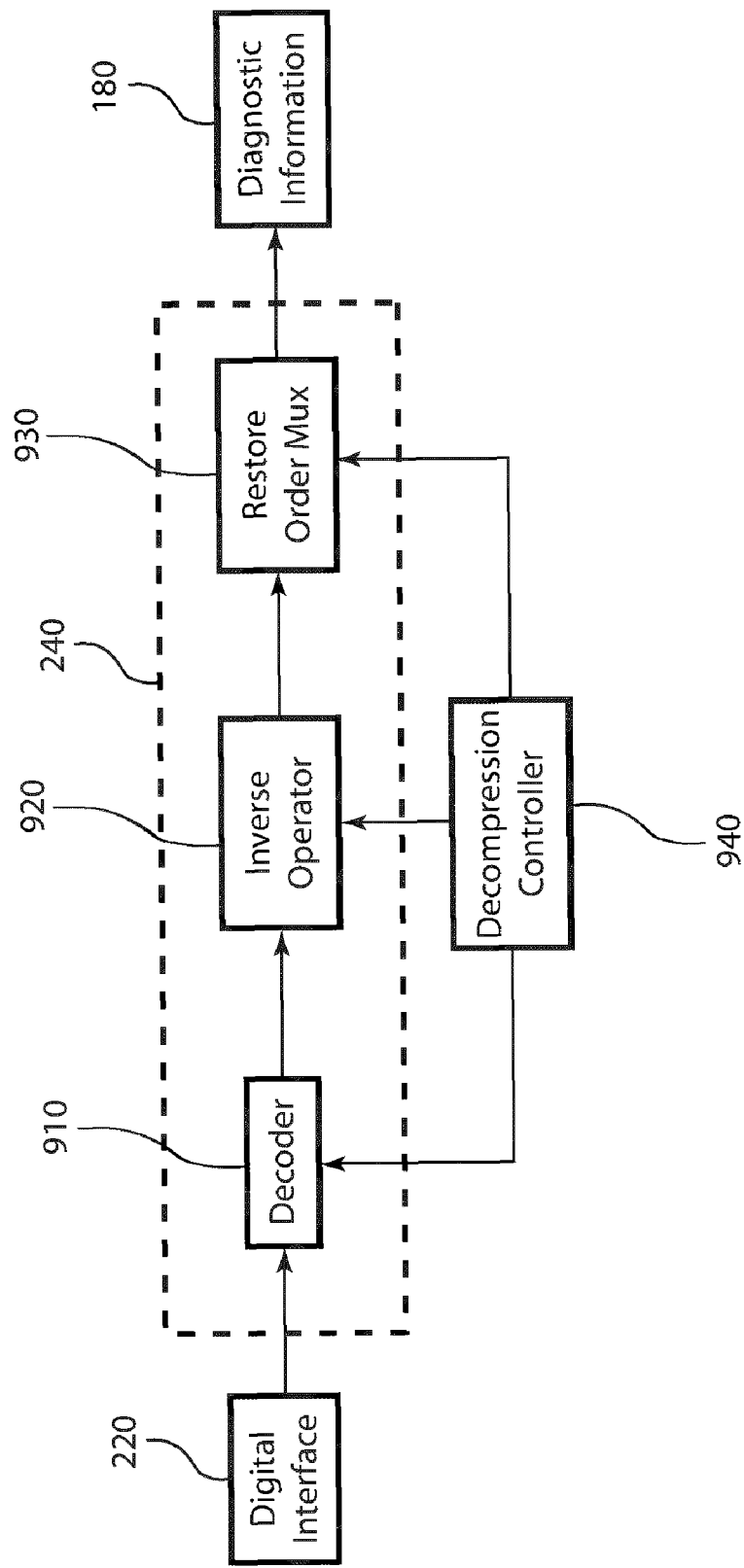
FIG. 21 is a block diagram of the operations performed by the decompressor 240 for the compression method described with respect to FIG. 18.

FIG. 21 is a block diagram of the operations performed by the decompressor 240 for the compression method described with respect to FIG. 18. The decoder 910 unpacks and performs decoding operations, for instance block floating point decoding, on the compressed data, to form decoded modified samples. The inverse arithmetic operator 920 performs the inverse operations to the arithmetic operator 830 to reconstruct the beamformed samples from the decoded modified samples. The multiplexer 930 restores the original sample order to the decompressed beamformed samples to form the corresponding decompressed beam. The decompression controller 940 provides control parameters to the decoder 910, the inverse operator 920 and the restore order multiplexer 930. The decompression controller 940 can extract control data from the header of the compressed data packet to determine the control parameters for the decompression operations.

The decompressor 240 of FIG. 21 can be applied to a multiplexed sequence of compressed groups of modified samples prior to demultiplexing the groups. The decoder 910 inverts the operations of the encoder 840 to decode the compressed groups forming groups of decoded modified samples in the group order. For block floating point decoding where the exponent tokens are differentially encoded, the decoder 910 uses the group order to integrate the exponent tokens to determine the n_exp values for the compressed groups corresponding to the same beam. The inverse operator 920 and the restore order multiplexer 930 also use the group order and n_exp to apply their respective operations to the groups of decoded modified samples corresponding to the same beam. The restore order multiplexer 930 reorders the decompressed beamformed samples within each group to the original sample order to form decompressed groups; however, decompressed groups are still in the group order. Referring to FIG. 13, the output of the restore order multiplexer corresponds to the decompressed groups $R_{ij}$ of the decompressed sequence 241. The group demultiplexer 254 separates the decompressed groups $R_{ij}$ into corresponding decompressed beams 253 and 255.

Figure 22:
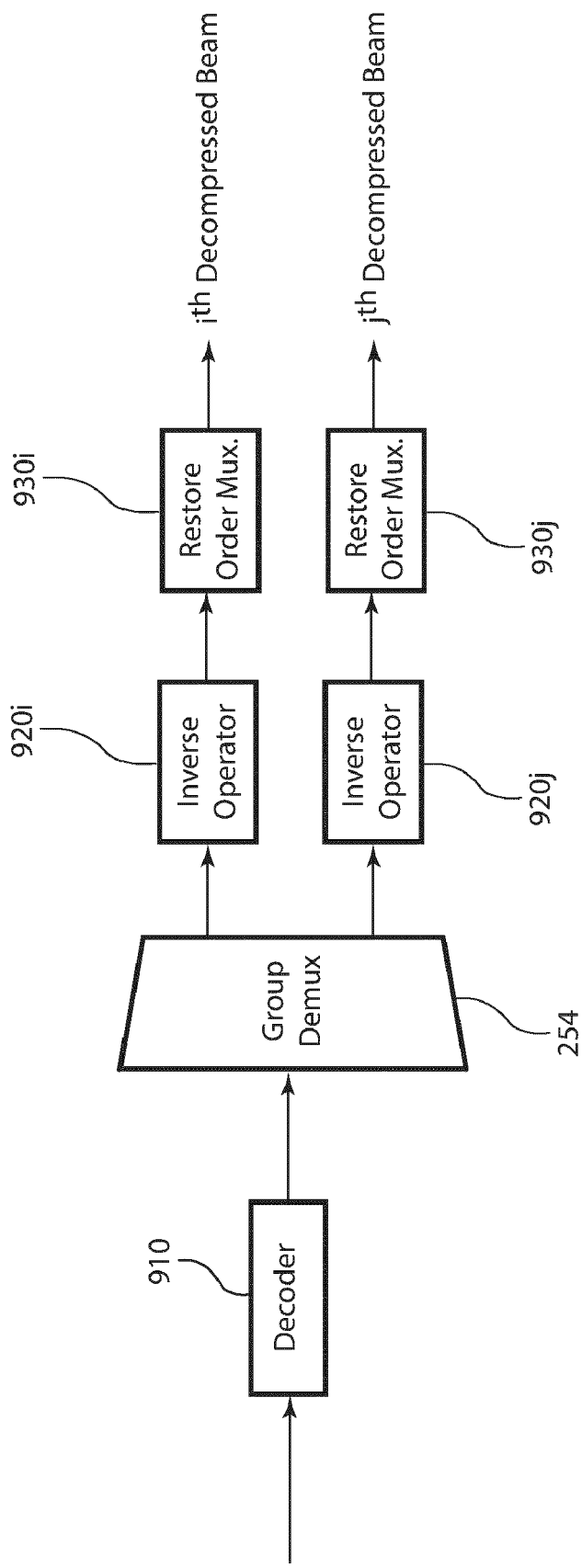
FIG. 22 is a block diagram of demultiplexing the groups of decoded modified samples.

Alternatively, the groups of decoded modified samples may be demultiplexed prior to the inverse operator 920, as shown in FIG. 22. The decoder 910 inverts the operations of the encoder 840 to unpack and decode the compressed groups to form corresponding groups of decoded difference samples in the group order. For block floating point decoding where the exponent token is differentially encoded, the decoder 910 uses the group order to integrate the exponent tokens to determine the n_exp values for the compressed groups corresponding to the same beam. The groups of decoded modified samples have the same number of bits per modified sample. The group demultiplexer 254 separates the groups of decoded modified samples to form an array of decoded modified samples corresponding to each beam. The inverse operators 920i and 920j are applied to the respective arrays of decoded modified samples and the restore order multiplexers 930i and 930j restore the original sample order to form the $i^{th}$ and $j^{th}$ decompressed beams, respectively.

The embodiments for the compressor 210 apply simple operations to the beamformed samples. The difference operator 330i (FIG. 14) includes one or more subtractors. The block floating point encoding (FIG. 7 and FIG. 11) uses comparators, subtractors and lookup tables. Alternatively, Huffman encoding uses a lookup table to assign a code to a value. The compression operations described with respect to FIG. 18 include demultiplexing, adding and subtracting. The embodiments for the decompressor 240 apply simple operations to decompress the compressed sample. The decompressor 240 includes lookup tables and adders for block floating point decoding. The integration operator 354 (FIG. 15) includes one or more adders for integrating the decoded samples. The operations of the decompressor 240 in FIG. 21 include adding, subtracting and multiplexing.

The preferred implementation of the present invention in an ultrasound system integrates the compressor 210 and the receive beamformer 160 in a single application specific integrated circuit (ASIC) device with input data channels coupled to receive the ultrasound signal samples from the ADC output channels 121i. The preferred implementation of the compressor 210 includes multiple compression cores in parallel, where each compression core is coupled to one of the beamformer output channels 161i and implements the compression operations of one compression unit 210a on the corresponding beam. Alternatively, one compression core can implement multiple compression units 210i to compress multiple beams. For this alternative, the compression core includes buffers to store beamformed samples corresponding to the different beams until they are processed. The beamforming and compression operations can also be implemented in a field programmable gate array (FPGA). The compressed beamformed samples can be output over LVDS ports 270i to the digital interface 220. The IP cores for LVDS interfaces are commercially available for ASIC and FPGA implementations. Alternative architectures include implementing the compressor 210 in a separate device from the receive beamformer 160. The compressor 210 can be implemented in an ASIC, FPGA or a programmable processor, such as a digital signal processor (DSP), microprocessor, microcontroller, multi-core CPU (such as IBM Cell), or graphics processing unit (GPU; such as Nvidia GeForce).

Depending on the ultrasound system architecture, the decompressor 240 may be incorporated into the same device as or a different device from the diagnostic information processor 180. The decompression operations can be implemented in an ASIC or FPGA. Alternatively, the decompression operations can be implemented in software or firmware programs executable by a programmable processor, such as a DSP, microprocessor, microcontroller, CPU or GPU. The preferred implementation of the decompressor 240 is a software program having instructions for the decompression operations executable by a GPU. The GPU may also be programmed to implement at least a portion of the operations of the diagnostic information processor 180 and scan converter 140. Alternatively, the decompressed beamformed samples may be transferred to another programmable processor, such as a CPU, for the additional signal processing operations.

Figure 23:
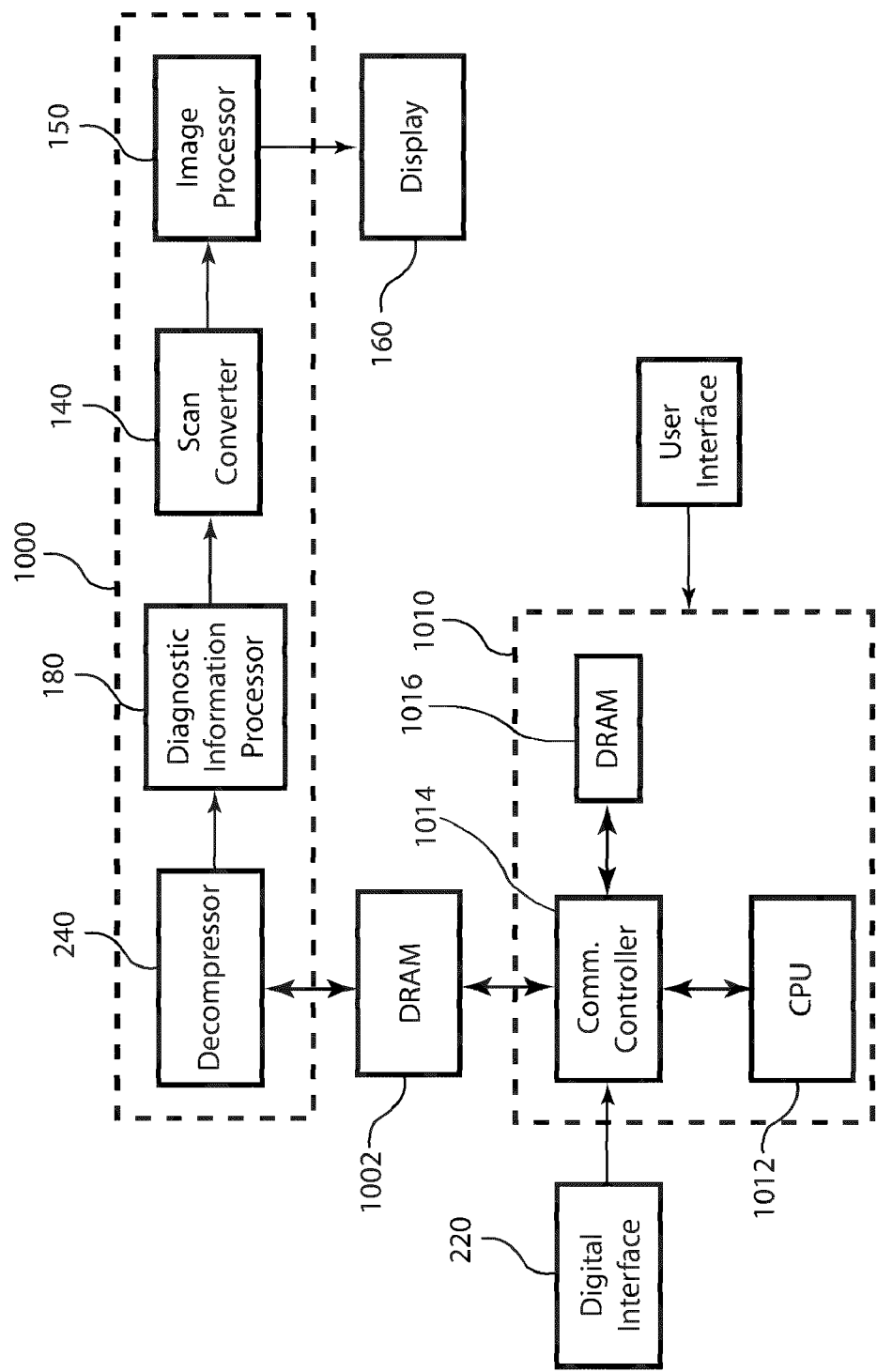
FIG. 23 is a block diagram of an implementation in a GPU of the decompressor and the other operations for generating an ultrasound image.

FIG. 23 is a block diagram of an implementation in a GPU of the decompressor 240 and the other operations for generating an ultrasound image. Current GPU architectures include multiple processing cores optimized for parallel calculations. For example, the Nvidia GeForce GTS 150 GPU includes 128 processing cores. Nvidia's "CUDA" (Compute Unified Device Architecture) is an application programming interface (API) that includes extensions to the C language for implementing parallel algorithms on the GPU's processing cores and is described in the document entitled "Getting Started with CUDA" by Ruetsch and Oster, Nvidia Corp., 2008. Alternative GPU and programming methodologies, such as OpenCL and Larrabee, described below, may provide the implementation platform. For the implementation depicted in FIG. 23, the GPU device 1000 may be programmed to execute the operations of the decompressor 240, the diagnostic information processor 180 (B-mode processing and Doppler processing), the scan converter 140 and the image processor 150. The GPU device 1000 may include a dynamic random access memory (DRAM) 1002 accessible by the parallel processing units. The DRAM 1002 may store compressed and/or decompressed beamformed samples and data resulting from the GPU's other processing operations. The system controller 1010 provides coordination of tasks for generating the ultrasound image from received data and responds to the user commands. The CPU 1012 may implement operations in support of decompression, such as decoding compression control parameters from the headers of compressed packets and providing them to the GPU device 1000 for configuring the decompression operations. The DRAM 1016 may store compressed beamformed samples received from the digital interface 220 and other data needed for the CPU operations. The communication controller 1014 directs the compressed packets received from the digital interface 220 to the DRAM 1002 or the DRAM 1016 and manages data exchange between the system controller 1010 and the GPU device 1000.

In a preferred system architecture, the system controller 1010 may be embodied in a motherboard of a computer having a screen for the display 160. The GPU device 1000 may be embodied in a graphics card, including the DRAM 1002, in communication with the system controller 1010 by a PCIe (Peripheral Component Interconnect Express) backplane link. Alternatively, the GPU device 1000 may be embodied in an IC mounted on the motherboard. In a system architecture where the ADC bank 120, receive beamformer 160 and compressor 210 are mounted in a data acquisition card, the digital interface 220 may be embodied by a PCIe backplane link.

It will be appreciated that, in accordance with Moore's Law, higher levels of integration will provide for more compact devices so that the system controller 1010 and the GPU device 1000 may be implemented in a single IC. For example, Intel Corporation is developing a many-core IC architecture that includes multiple instantiations of an x86 CPU core augmented with a vector processing unit. The architecture, referred to as Larrabee, is described in the document entitled "Larrabee: A Many-Core x86 Architecture for Visual Computing" by Seiler et al., ACM Transactions on Graphics, Vol. 27, No. 3, Article 18, August 2008. The Larrabee architecture supports applications requiring parallel processing, including graphics processing. The "Larrabee Native" programming model includes a C/C++ and APIs for parallel programming and vectorization.

Figure 24:
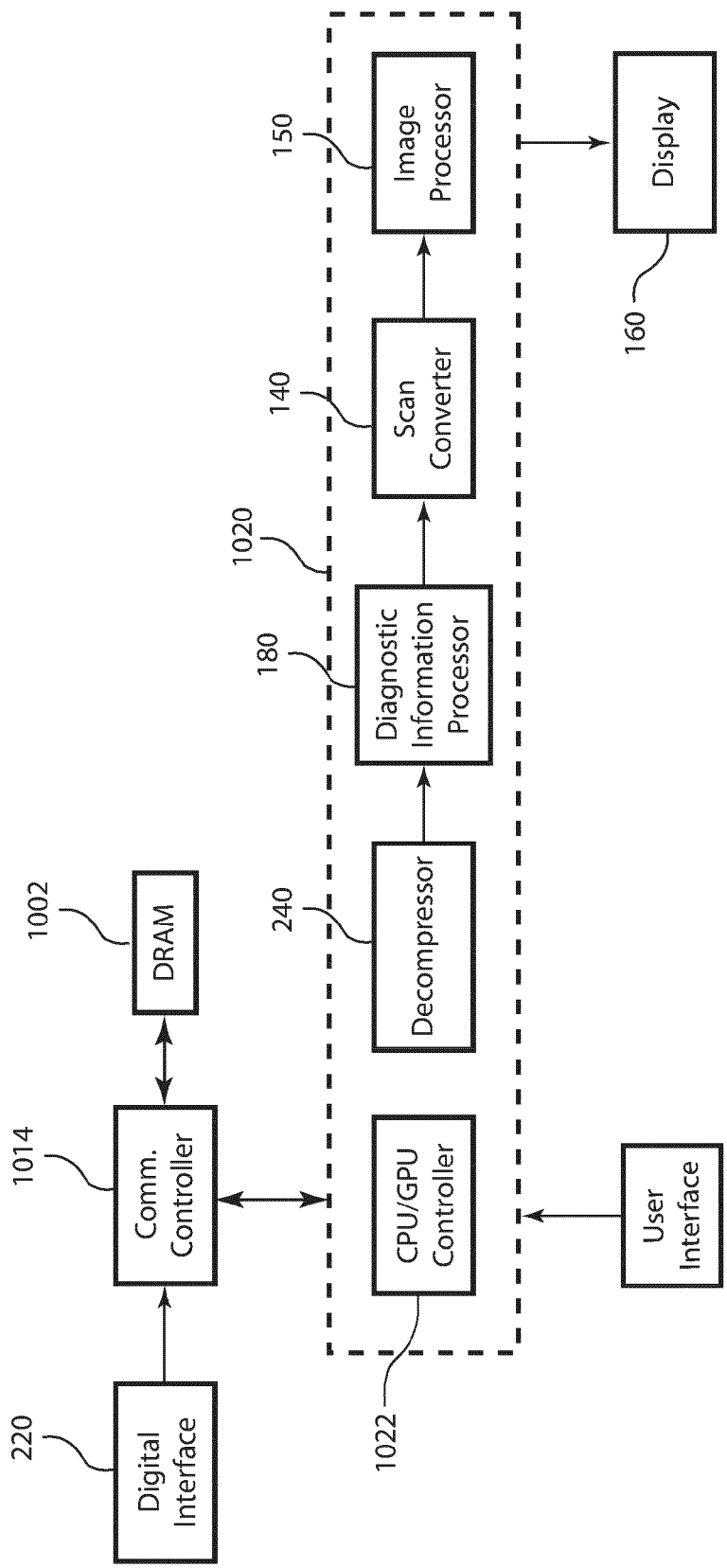
FIG. 24 is a block diagram of an implementation in a CPU/GPU device of the decompressor and the other operations for generating an ultrasound image.

FIG. 24 is a block diagram of an implementation in a CPU/GPU device of the decompressor 240 and the other operations for generating an ultrasound image. The CPU/GPU device 1020 may implement the operations of the decompressor 240, the diagnostic information processor 130, the scan converter 140 and the image processor 150. The CPU/GPU controller 1022 coordinates the processing operations on the compressed beamformed samples received from the digital interface 220 and responds to user input. The CPU/GPU device 1020 may be implemented by the Larrabee platform or other programmable device with integrated CPU and GPU functionality.

In a system architecture where the ADC bank 120, the receive beamformer 160 and compressor 210 are housed in the transducer head, the digital interface 220 may be a wired or a wireless communication link. For a wired communication link, the digital interface may be implemented by a PCIe cable link or an optical fiber link. For a wireless communication link, the digital interface may provide digital modulation and transmission of the compressed packets via a radio frequency channel and digital demodulation of the received compressed packets. The wireless link may comply with a wireless communication protocol, such as WiFi (IEEE 802.11) or an UWB (ultra-wideband) format.

While the preferred embodiments of the invention have been illustrated and described, it will be clear that the invention is not limited to these embodiments only. Numerous modifications, changes, variations, substitutions and equivalents will be apparent to those skilled in the art, without departing from the spirit and scope of the invention, as described in the claims.

I claim:

1. In an ultrasound imaging system including a receive beamformer applied to a plurality of sequences of ultrasound signal samples received during a sampling window to form one or more beams, wherein each beam is represented by an array of beamformed samples, wherein analog to digital conversion of a plurality of analog ultrasound signals output by a plurality of ultrasound transducer elements during the sampling window produce the plurality of sequences of ultrasound signal samples, a method comprising:
   compressing the beams produced by applying the receive beamformer to the ultrasound signal samples received during the sampling window to form compressed beams, including compressing the beamformed samples in the array representing a particular beam to form compressed beamformed samples for a corresponding compressed beam, wherein the compressing of a particular beamformed sample in the array depends in part on a characteristic of at least one other beamformed sample in the array, wherein each beam is compressed independently of another beam corresponding to the sampling window, wherein the corresponding compressed beam includes fewer bits than the particular beam; and
   transferring the compressed beams across a digital interface to a signal processor.

2. The method of claim 1, wherein the arrays of beamformed samples are downconverted to an intermediate frequency or to a baseband prior to the step of compressing.

3. The method of claim 1, further comprising:
   decompressing at least a portion of the compressed beamformed samples of the corresponding compressed beam received from the digital interface to form decompressed beamformed samples for a corresponding decompressed beam, wherein the decompressing is applied to the corresponding compressed beam independently of another compressed beam, wherein the signal processor further processes the decompressed beamformed samples.

4. The method of claim 1, wherein the step of compressing applies block floating point encoding to the array of beamformed samples representing the particular beam to form the corresponding compressed beam.

5. The method of claim 4, further comprising:
   decompressing at least a portion of the compressed beamformed samples received from the digital interface by applying block floating point decoding to a corresponding portion of the corresponding compressed beam to form decompressed beamformed samples for a decompressed beam, wherein the signal processor further processes the decompressed beamformed samples.

6. The method of claim 1, wherein the step of compressing further comprises:
   defining groups of consecutive beamformed samples in the array of beamformed samples corresponding to the particular beam, each group having a predetermined number of beamformed samples;
   determining an exponent value for the beamformed sample having a maximum magnitude in the group;

encoding the exponent value for the group to form an exponent token;

forming a mantissa having a reduced number of bits to represent each beamformed sample in the group, wherein the reduced number of bits is based on the exponent value; and representing compressed beamformed samples of the group using the exponent token and a predetermined number of mantissas to form a corresponding compressed group, wherein a plurality of compressed groups form the corresponding compressed beam.

7. The method of claim 6, wherein the step of forming a mantissa further comprises:

removing a number of least significant bits (LSBs) from each beamformed sample in the group by truncating or rounding the beamformed sample to form a reduced mantissa, wherein the number of LSBs removed is based on the exponent value, wherein the step of representing the compressed beamformed samples uses the exponent token and the predetermined number of reduced mantissas to form the corresponding compressed group.

8. The method of claim 6, wherein the receive beamformer produces J beams, where J is at least two, wherein the groups of beamformed samples of the corresponding beam are in an original group order, the method further comprising:

multiplexing the compressed groups corresponding to the J beams to form M multiplexed sequences of compressed groups where M is less than J, including interleaving the compressed groups corresponding to a set of at least two of the compressed beams to form a corresponding multiplexed sequence, wherein the compressed groups in the corresponding multiplexed sequence are arranged in a group order, wherein the step of transferring transfers the M multiplexed sequences.

9. The method of claim 8, further comprising:

decompressing the compressed groups of the corresponding multiplexed sequence received from the digital interface to form decompressed groups containing decompressed beamformed samples, wherein the decompressed groups are in the group order of the corresponding multiplexed sequence; and demultiplexing the decompressed groups of the corresponding multiplexed sequence to form a set of decompressed beams corresponding to the set of the compressed beams, including rearranging the decompressed groups from the group order to restore the original group order to the decompressed beams, wherein the decompressed beams are provided for further signal processing.

10. The method of claim 6, further comprising:

decompressing at least a portion of the compressed beamformed samples received from the digital interface by selecting the corresponding compressed groups for decompression to form corresponding groups of decompressed beamformed samples provided for further signal processing.

11. In an ultrasound imaging system including a receive beamformer applied to a plurality of sequences of ultrasound signal samples received during a sampling window to form one or more beams, wherein each beam is represented by an array of beamformed samples, wherein analog to digital conversion of a plurality of analog ultrasound signals output by a plurality of ultrasound transducer elements during the sampling window produce the plurality of sequences of ultrasound signal samples, a method comprising:

compressing the beams formed by applying the receive beamformer to the ultrasound signal samples received during the sampling window to form compressed beams, wherein each beam is compressed independently of another beam corresponding to the sampling window, the compressing including:

calculating differences between consecutive beamformed samples in the array representing a particular beam to form a corresponding sequence of difference samples, wherein the differences are first order or higher order differences; and encoding the corresponding sequence of difference samples to form the compressed beamformed samples of a corresponding compressed beam, wherein the corresponding compressed beam includes fewer bits than the particular beam; and transferring the compressed beams across a digital interface to a signal processor.

12. The method of claim 11, wherein the array of beamformed samples are downconverted to a baseband or an intermediate frequency prior to the step of compressing.

13. The method of claim 11, wherein the step of calculating differences further comprises:

calculating differences between the beamformed samples in pairs of beamformed samples in the array separated by a predetermined number of sample intervals to form a corresponding sequence of difference samples; and encoding the corresponding sequence of difference samples to form the compressed beamformed samples of the corresponding compressed beam.

14. The method of claim 13, further comprising:

selectively inverting one of the beamformed samples in each pair of beamformed samples separated by the predetermined number of sample intervals in accordance with an inversion control parameter prior to the step of calculating differences.

15. The method of claim 11, further comprising decompressing at least a portion of the compressed beamformed samples received from the digital interface, the decompressing further comprising:

decoding the compressed beamformed samples of the corresponding compressed beam to form decoded difference samples; and integrating the decoded difference samples to form decompressed beamformed samples for a corresponding decompressed beam, wherein the integrating calculates first order or higher order integrations to invert the difference operations of the step of calculating differences.

16. The method of claim 11, wherein the step of encoding applies block floating point encoding to the corresponding sequence of difference samples to form the corresponding compressed beam.

17. The method of claim 16, further comprising decompressing at least a portion of the compressed beamformed samples received from the digital interface, the decompressing further comprising:

decoding the compressed beamformed samples by applying block floating point decoding to the compressed beamformed samples of the corresponding compressed beam to form decoded difference samples; and integrating the decoded difference samples to form decompressed beamformed samples for a corresponding decompressed beam, wherein the integrating calculates first order or higher order integrations to invert the first order or higher order differences of the step of calculating differences.

18. The method of claim 11, wherein the step of encoding further comprises:

defining groups of consecutive difference samples in the corresponding sequence of difference samples, each group having a predetermined number of difference samples;
determining an exponent value for the difference sample having a maximum magnitude in the group;
encoding the exponent value for the group to form an exponent token;
forming a mantissa having a reduced number of bits to represent each difference sample in the group, wherein the reduced number of bits is based on the exponent value; and
representing the difference samples of the group using the exponent token and a predetermined number of mantissas to form a corresponding compressed group, wherein a plurality of compressed groups form the corresponding compressed beam.

19. The method of claim 18, wherein the step of forming a mantissa further comprises:
removing a number of least significant bits (LSBs) from each difference sample in the group by truncating or rounding the difference sample to form a reduced mantissa, wherein the number of LSBs removed is based on the exponent value, wherein the step of representing the difference samples uses the exponent token and the predetermined number of reduced mantissas to form the corresponding compressed group.

20. The method of claim 18, wherein the receive beamformer produces N beams, where N is at least two, wherein the groups of difference samples of the corresponding beam are in an original group order, the method further comprising:
multiplexing the compressed groups corresponding to the N compressed beams to form M multiplexed sequences of compressed groups where M is less than N, including interleaving the compressed groups corresponding to a set of at least two of the compressed beams to form a corresponding multiplexed sequence, wherein the compressed groups in the corresponding multiplexed sequence are arranged in a group order, wherein the step of transferring transfers the M multiplexed sequences.

21. The method of claim 20, further comprising:
decoding the compressed groups of the corresponding multiplexed sequence received from the digital interface to form decoded groups of decoded difference samples, wherein the decoded groups are in the group order;
integrating the decoded difference samples corresponding to the same compressed beam in accordance with the group order to form decompressed groups containing decompressed beamformed samples, wherein the decompressed groups are in the group order of the corresponding multiplexed sequence; and
demultiplexing the decompressed groups of the corresponding multiplexed sequence to form a set of decompressed beams corresponding to the set of the compressed beams, including rearranging the decompressed groups from the group order to restore the original group order to the decompressed beams, wherein the decompressed beams are provided for further signal processing.

22. The method of claim 20, further comprising:
decoding the compressed groups of the corresponding multiplexed sequence received from the digital interface to form decoded groups containing decoded difference samples, wherein the decoded groups are in the group order of the corresponding multiplexed sequence;
demultiplexing the decoded groups to form a set of sequences of decoded difference samples corresponding to a set of the compressed beams, including rearranging the decoded groups from the group order to restore the original group order to the sequences of decoded difference samples; and
integrating each sequence of decoded difference samples to form decompressed beamformed samples for a corresponding decompressed beam, wherein the integrating calculates first order or higher order integrations to invert the first order or higher order differences of the step of calculating differences.

23. The method of claim 18, further comprising:
decompressing at least a portion of the compressed beamformed samples received from the digital interface by selecting the corresponding compressed groups for decompression to form corresponding groups of decompressed beamformed samples provided for further signal processing.

24. In an ultrasound imaging system including a receive beamformer applied to a plurality of sequences of ultrasound signal samples received during a sampling window to form one or more beams, wherein each beam is represented by an array of beamformed samples, wherein a plurality of analog to digital converters samples a plurality of analog ultrasound signals output by a plurality of ultrasound transducer elements during the sampling window produce the plurality of sequences of ultrasound signal samples provided to the receive beamformer, an apparatus comprising:
a compressor coupled to the receive beamformer to receive the one or more arrays of beamformed samples formed by applying the receive beamformer to the ultrasound signal samples received during the sampling window, the compressor including one or more compression units, wherein a corresponding compression unit compresses the beamformed samples of a corresponding beam independently of another beam corresponding to the sampling window to form compressed beamformed samples of a corresponding compressed beam, wherein the corresponding compression unit is configured to compress a particular beamformed sample of a particular beam based in part on a characteristic of at least one other beamformed sample of the corresponding beam, wherein the corresponding compressed beam includes fewer bits than the particular beam, wherein the compressor provides the compressed beams to a digital interface for transfer to a signal processor.

25. The apparatus of claim 24, further comprising:
one or more downconverters coupled between the receive beamformer and the compressor, each downconverter receiving a corresponding beam from the receive beamformer and converting the beamformed samples of the corresponding beam to an intermediate frequency or to a baseband to form a downconverted beam provided to the corresponding compression unit.

26. The apparatus of claim 24, further comprising:
a decompressor coupled to receive the compressed beams from the digital interface and providing decompressed beams to the signal processor, wherein the decompressor decompresses the compressed beamformed samples of a particular compressed beam independently of another compressed beam corresponding to the sampling window to form decompressed beamformed samples of a corresponding decompressed beam.

27. The apparatus of claim 26, wherein the decompressor is implemented in a field programmable gate array (FPGA).

28. The apparatus of claim 26, wherein the signal processor is implemented in a FPGA, the FPGA further including:
a decompression core implementing the decompressor;

data channels for receiving the compressed beams from the digital interface to provide the compressed beamformed samples to the decompression core; and
data channels for providing the decompressed beams to the signal processor.

29. The apparatus of claim 26, wherein the decompressor is implemented at least partially in a graphics processing unit (GPU).

30. The apparatus of claim 29, wherein the signal processor is implemented at least partially in the GPU.

31. The apparatus of claim 24, wherein the compression unit further comprises:
a block floating point encoder applied to the array of beamformed samples to produce the corresponding compressed beam.

32. The apparatus of claim 31, further comprising:
a decompressor receiving the compressed beams from the digital interface and providing decompressed beams to the signal processor, the decompressor including a block floating decoder applied to at least a portion of compressed beamformed samples of the corresponding compressed beam to form decompressed beamformed samples of a corresponding decompressed beam.

33. The apparatus of claim 24, wherein the compression unit further comprises:
a difference operator to calculate first or higher order differences between consecutive beamformed samples of the corresponding beam to produce a sequence of difference samples; and
an encoder to encode the sequence of difference samples to form the compressed beamformed samples of the corresponding compressed beam.

34. The apparatus of claim 33, wherein the difference operator calculates the differences between the beamformed samples in pairs of beamformed samples of the corresponding beam, wherein the beamformed samples of each pair are separated by a predetermined number of sample intervals to form the sequence of difference samples.

35. The apparatus of claim 33, further comprising a decompressor receiving the compressed beams from the digital interface and providing decompressed beams to the signal processor, the decompressor including:
a decoder applied to at least a portion of the compressed beamformed samples of the corresponding compressed beam to produce a sequence of decoded difference samples; and
an integrator for calculating first or higher order integrals of the sequence of decoded difference samples to form decompressed beamformed samples of a corresponding decompressed beam.

36. The apparatus of claim 34, wherein the compression unit further comprises:
an inverter that selectively inverts one of the beamformed samples in each pair of beamformed samples separated by the predetermined number of sample intervals in accordance with an inversion control parameter to produce the pairs of beamformed samples for the difference operator.

37. The apparatus of claim 24, wherein the receive beamformer provides J beams to J compression units to form J compressed beams, wherein the corresponding compression unit produces a plurality of compressed groups of compressed beamformed samples for the corresponding compressed beam, wherein the compressed groups are in an original group order, each compressed group having a predetermined number of compressed beamformed samples, the apparatus further comprising:
a group multiplexer receiving the J compressed beams and providing M multiplexed sequences of compressed groups to the digital interface, where M is less than J, the group multiplexer interleaving the groups of compressed samples corresponding to a set of at least two compressed beams to form a corresponding multiplexed sequence, wherein the compressed groups in the corresponding multiplexed sequence are arranged in a group order.

38. The apparatus of claim 37, further comprising:
a decompressor receiving the M multiplexed sequences from the digital interface and forming M sequences of decompressed groups, wherein the decompressor decompresses the compressed groups of the corresponding multiplexed sequence to form decompressed groups in the group order; and
a group demultiplexer coupled to receive the M sequences of decompressed groups and providing J decompressed beams to the signal processor, wherein the decompressed groups of the corresponding multiplexed sequence are rearranged from the group order to the original order to form a set of decompressed beams corresponding to the set of compressed beams.

39. The apparatus of claim 24, wherein the compressor is implemented in an application specific integrated circuit (ASIC) or a field programmable gate array (FPGA).

* * * * *